US005763172A

United States Patent [19]

Magda et al.

[11] Patent Number: 5,763,172

[45] Date of Patent: Jun. 9, 1998

[54] METHOD OF PHOSPHATE ESTER HYDROLYSIS

[75] Inventors: Darren Magda, Cupertino, Calif.; Jonathan L. Sessler, Austin, Tex.; Meredith Wright, San Jose, Calif.; Richard A. Miller, Portola Valley; William C. Dow, Fremont, both of Calif.

[73] Assignees: Board of Regents, The University of Texas System, Austin, Tex.; Pharmacyclics, Inc., Sunnyvale, Calif.

[21] Appl. No.: 486,962

[22] Filed: Jun. 7, 1995

Related U.S. Application Data

[63] Continuation of Ser. No. 485,581, Jun. 7, 1995, abandoned, which is a continuation-in-part of Ser. No. 452,261, filed as PCT/US94/06284 Jun. 9, 1994, abandoned, which is a continuation-in-part of Ser. No. 227,370, Apr. 14, 1994, Pat. No. 5,559,207, which is a continuation-in-part of Ser. No. 75,123, Jun. 9, 1993, abandoned, which is a continuation-in-part of Ser. No. 822,964, Jan. 21, 1992, Pat. No. 5,252, 720.

[51] Int. Cl.$^6$ .............................. C12Q 1/68; C07H 19/00; A01N 61/00

[52] U.S. Cl. ............................ 435/6; 536/22.1; 536/23.1; 536/24.3; 536/25.32; 514/1; 514/44

[58] Field of Search ............................... 435/6; 536/22.1, 536/23.1, 24.3, 25.32; 514/1, 44

[56] References Cited

U.S. PATENT DOCUMENTS

| | | | |
|---|---|---|---|
| 4,318,825 | 3/1982 | Frame | 252/428 |
| 4,647,447 | 3/1987 | Gries et al. | 524/9 |
| 4,835,263 | 5/1989 | Nguyen et al. | 536/27 |
| 4,878,891 | 11/1989 | Judy et al. | 604/5 |
| 4,880,008 | 11/1989 | Lauffer | 128/654 |
| 4,883,790 | 11/1989 | Levy et al. | 540/145 |
| 4,899,755 | 2/1990 | Lauffer et al. | 128/654 |

(List continued on next page.)

FOREIGN PATENT DOCUMENTS

| | | |
|---|---|---|
| 0111418 | 6/1984 | European Pat. Off. . |
| 0196515 | 10/1986 | European Pat. Off. . |
| 0233701 A2 | 8/1987 | European Pat. Off. . |
| 90/01208 | 8/1990 | WIPO . |
| WO 90/10633 | 9/1990 | WIPO . |
| 91/19730 | 12/1991 | WIPO . |
| 92/01781 | 2/1992 | WIPO . |
| WO 93/14093 | 7/1993 | WIPO . |
| WO94/09003 | 4/1994 | WIPO . |
| WO 94/29316 | 12/1994 | WIPO . |

OTHER PUBLICATIONS

Abid et al., "Lanthanide Complexes of Some Macrocyclic Schiff Bases Derived from Pyridine-2,6-dicarboxaldehyde and α,ω-Primary Diamines", *Inorg. Chim. Acta*, 95:119–125, 1984.

Acholla et al., "Binucleating Tetrapyrrole Macrocycles", *J. Am. Chem. Soc.*, 107:6902–6908, 1985.

Acholla et al., "A Binucleating Accordian Tetrapyrrole Macrocycle", *Tetrahedron Lett.*, 25:3269–3270, 1984.

Ansell, "X-Ray Crystal Structure of the Pentagonal Bipyramidal Nickel(11) Complex $[Ni^{11}(L)(H_2O)_2](BF_4)_2$ and the Selective Stabilisation of the Nickel (1) Oxidation State by a Quinquedentate Macrocyclic Ligand", *J. Chem. Soc., Chem. Commun.* pp. 546–547, 1982.

(List continued on next page.)

*Primary Examiner*—Ardin H. Marschel
*Assistant Examiner*—Jezia Riley
*Attorney, Agent, or Firm*—Arnold, White & Durkee; Jacqueline S. Larson

[57] ABSTRACT

A method of phosphate ester hydrolysis including incubating a solution of an aqueous phosphate ester with a metal-lotexaphyrin complex under conditions and for a time sufficient to hydrolyze the phosphate ester. The metal is a metal cation having catalytic activity for ester bond hydrolysis in aqueous solution. Phosphate ester substrates include nucleic acid such as RNA, phosphoric anhydrides, phospholipids, and alkyl phosphate esters.

28 Claims, 6 Drawing Sheets

SEQ. ID. NO. 1
5'-EuTx-NH-$(CH_2)_6$-$PO_4$-CTC GGC CAT AGC GAA TGT TC-3' $10_A$ $(9_D)$
3'-pC*C ACU GUA GAA GAG CCG GUA UCG CUU ACA AG-5' $10_B$
SEQ. ID. NO. 3

SEQ. ID. NO. 2
5'-DyTxNH-$(CH_2)_6$-$PO_4$-CAT CTG TGA GCC GGG TGT TG-3' $10_C$ $(9_I)$
3'-A AAU AAA ACC UCU GAAGUA GAC ACU CGG CCC ACA AC-5' $10_D$
SEQ. ID. NO. 11

U.S. PATENT DOCUMENTS

| | | | |
|---|---|---|---|
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,141,911 | 8/1992 | Meunier et al. | 502/159 |
| 5,162,509 | 11/1992 | Sessler et al. | 534/15 |
| 5,242,797 | 9/1993 | Hirschfeld | 435/7 |
| 5,252,720 | 10/1993 | Sessler et al. | 534/11 |
| 5,256,399 | 10/1993 | Sessler et al. | 424/9 |
| 5,272,056 | 12/1993 | Burrows et al. | 435/6 |
| 5,272,142 | 12/1993 | Sessler et al. | 514/185 |
| 5,292,414 | 3/1994 | Sessler et al. | 204/157.5 |
| 5,302,714 | 4/1994 | Sessler et al. | 540/472 |
| 5,369,101 | 11/1994 | Sessler et al. | 534/13 |
| 5,371,199 | 12/1994 | Therien et al. | 534/11 |
| 5,432,171 | 7/1995 | Sessler et al. | 514/185 |
| 5,439,570 | 8/1995 | Sessler et al. | 254/157.17 |
| 5,451,576 | 9/1995 | Sessler et al. | 514/185 |
| 5,457,183 | 10/1995 | Sessler et al. | 534/11 |

OTHER PUBLICATIONS

Bauer et al., "Sapphyrins: Novel Aromatic Pentapyrrolic Macrocycles", *J. Am. Chem. Soc.*, 105:6429–6436, 1983.

Broadhurst et al., "Preparation of Some Sulphur–containing Polypyrrolic Macrocycles. Sulphur Extrusion from a meso–Thiaphlorin", *J. Chem. Soc., Chem. Commun.* pp. 807–809, 1970.

Broadhurst et al., "18–and 22–π–Electron Macrocycles Containing Furan, Pyrrole, and Thiophen Rings", *J. Chem. Soc., Chem. Commun.* pp. 1480–1482, 1969.

Broadhurst et al., "New Macrocyclic Aromatic Systems Related to Porphins", *J. Chem. Soc., Chem. Commun.* pp. 23–24, 1969.

Cuellar et al., "Synthesis and Characterization of Metallo and Metal–Free Octaalkylphthalocyanines and Uranyl Decaalkysuperphthalocyanines", *Inorg. Chem.*, 20:3766–3770, 1981.

Day et al., "Large Metal Ion–Centered Template Reactions. A Uranyl Complex of Cyclopentakis (2–iminoisoindoline)", *J. Am. Chem. Soc.*, 97:4519–4527, 1975.

De Cola et al., "Hexaaza Macrocyclic Complexes of the Lanthanides", *Inorg. Chem.*, 25:1729–1732, 1986.

Dougherty, "Photosensitizers: Therapy and Detection of Malignant Tumors", *Photochem. Photobiol.*, 45:879–889, (1987).

Gosmann et al., "Synthesis of a Fourfold Enlarged Porphyrin with an Extremely Large, Diamagnetic Ring–Current Effect", *Angew. Chem., Int. Ed Engl.*, 25:1100–1101, (1986).

Lauffer, "Paramagnetic Metal Complexes as Water Proton Relaxation Agents for NMR Imaging: Theory and Design", *Chem. Rev.*, 87:901–927, 1987.

LeGoff et al., "Synthesis of a [1,5,1,5] Platyrin, a 26 π–Electron Tetrapyrrolic Annulene", *J. Org. Chem.*, 52:710–711, 1987.

Marks et al., "Large Metal Ion–Centered Template Reactions. Chemical and Spectral Studies of the Superphthalocyanine Dioxocyclopentakis (1–iminoisoindolinato) uranium (VI) and Its Derivatives", *J. Am. Chem. Soc.*, 100:1695–1705, 1978.

Rexhausen et al., "The Synthesis of a New 22 π–Electron Macrocycle: Pentaphyrin". *J. Chem. Soc., Chem. Commun.*, pp. 275, 1983.

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate Porphyrin–Like Ligands", *Comm. Inorg. Chem.*, 7:333–350, 1988.

Sessler et al., "An Expanded Porphyrin: The Synthesis and Structure of a New Aromatic Pentadentate Ligand", *J. Am. Chem. Soc.*, 110:5586–5588, 1988.

Tweedle et al., "Principles of Contrast–Enhanced MRI, in Magnetic Resonance Imaging," 2nd ed. Partain, et al. Eds., W. B. Saunders: Philadelphia, vol. I (1988) 793–809.

Vogel et al., "Porphycene—a Novel Porphin Isomer", *Angew. Chem., Int. Ed. Engl.*, 25:257–259, 1986.

Vogel et al., "2,7,12,17–Tetrapropylporphycene—Counterpart of Octaethylporphyrin in the Porphycene Series", *Angew. Chem., Int. Ed. Engl.*, 26:928–931, 1987.

Sessler et al., "A Wafer–Stable Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadmium Expanded Porphyrin: Solution and X–ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. Soc., Chem. Commun.*, 314–316, 1989. Submitted as A32 in 1449 for UTSB:458.

Sessler et al., "Expanded Porphyrins: The synthesis and Metal Binding Properties of Novel Tripyrrane–Containing Macrocycles", *J. Coord. Chem.*, 18:99–104, 1988.

Sessler et al., "The Synthesis and Structure of a Novel 22 π–Electron Aromatic Pentadentate Macrocyclic Ligand: An Expanded Porphyrin", Toronto ACS Meeting, Jun. 1988. USA.

Sessler et al., "A Water–Stable Gadolinium (III) Complex Derived from a New Pentadentate", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived (Texaphyrin–type) Macrocycles: Potential Photosensitizers Which Absorb in the Far–red Spectral Region", *SPIE, Optical Methods for Tumor Treatment and Early Diagnosis: Mechanism and Technique*, 1426:318–329, 1991.

Sessler et al., "'Texaphyrin': A Novel 22 π–Electron Aromatic Pentadentate Macrocyclic Ligand", *ACS meeting*, Los Angeles, Sep. 1988.

Sessler and Burrell, "Expanded Porphyrins," *Topics in Current Chemistry*, 161:180–273, 1991.

"2–Äthylamino–2–methyl–propanol–(1)", *Beilstein's Handbuch*, 4:785, 1950.

"Tentative Rules for Carbohydrate Nomenclature Part 1 (1969)," *Handbook of Biochemistry and Molecular Biology*, 3rd ed., Fasman, Ed., CRC Press, Cleveland, Ohio, pp. 100–102.

Sessler et al., "Preparation of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Washington, DC.

Sessler et al., "Synthesis and Applications of Schiff–Base Derived Expanded Porphyrins," *Abstracts of Papers*, Part 1, 204th ACS National Meeting, Aug. 23–28, 1992, Washington, DC.

Sessler, Jonathan L., "Texas–Sized Molecule," *Discovery*, 13(1):44–49, 1993.

Sessler et al., "Photodynamic Inactivation of Enveloped Viruses Using Sapphyrin, α 22 π–Electron Expanded Porphyrin: Possible Approaches to Prophylactic Blood Purification Protocols," *SPIE Photodynamic Therapy: Mechanisms II*, 1203:233–245, 1990.

Maiya et al., "Ground–and Excited–State Spectral and Redox Properties of Cadmium(II) Texaphyrin," *Journal of Physical Chemistry*, 93(24):8111–8115, 1989.

Sessler et al., "Texaphyrins: Synthesis and Applications," *Accounts of Chemical Research*, 27(2):43–50, 1994.

Young et al., "Preclinical Evaluation of Gadolinium (III) Texaphyrin Complex. A New Paramagnetic Contrast Agent for Magnetic Resonance Imaging," *Investigative Radiology*, 29(3):330–338, 1994.

Dietrich et al., "Proton Coupled Membrane Transport of Anions Mediated by Cryptate Carriers," *J. Chem. Soc. Chem. Comm.*, 1988, 11:691–692.

Dixon et al., "Molecular Recognition: Bis–Acylguanidiniums Provide a Simple Family of Receptors for Phosphodiesters," *J. Am. Chem. Soc.*, 1992, 114:365–366.

Furuta et al., "Enhanced Transport of Nucleosides and Nucleoside Analogues with Complementary Base–Pairing Agents," *Journal of the American Chemical Society*, 1991, 113:4706–4707.

Galán et al., "A Synthetic Receptor for Dinucleotides," *J. Am. Chem. Soc.*, 1991, 113:9424–9425.

Galán et al., "Selective Complexation of Adenosine Monophosphate Nucleotides By Rigid Bicyclic Guanidinium Abiotic Receptors," *Tetrahedron Letters*, 32(15):1827–1830, 1991.

Hisatome et al., "Porphyrins Coupled with Nucleoside Bases. Synthesis and Characterization of Adenine–and Thymine–Porphyrin Derivatives," *Chemistry Letters*, 1990, 2251–2254.

Hosseini et al., "Multiple Molecular Recognition and Catalysis. A Multifunctional Anion Receptor Bearing an Anion Binding Site, an Intercalating Group, and a Catalytic Site for Nucleotide Binding and Hydrolysis," *J. Am. Chem. Soc.*, 1990, 112:3896–3904.

Hosseini et al., "Multiple Molecular Recognition and Catalysis. Nucleotide Binding and ATP Hydrolysis by a Receptor Molecule Bearing an Anion Binding Site, an Intercalcator Group, and a Catalytic Site," *J. Chem. Soc. Chem. Commun.*, 1988, 9:596–598.

Kimura et al., "A Study of New Bis(macrocyclic polyamine) Ligands as Inorganic and Organic Anion Receptors," *J. Org. Chem.*, 1990, 55(1):46–48.

Li and Diederich, "Carriers for Liquid Membrane Transport of Nucleotide 5'–Triphosphates," *J. Org. Chem.*, 1992, 47:3449–3454.

Marks and Stojakowvic, "Large Metal Ion–Centered Template Reactions. Chemical and Spectral Studies of the Superphthalocyanine Dioxocyclopentakis (1–iminoisoindolinato) uranium(VI) and Its Derivatives," *J. Am. Chem. Soc.*, 1978, 1695–1705.

Schmidtchen, "A Non–Macrocyclic Host for Binding Organic Phosphates in Protic Solvents," *Tetrahedron Letters*, 1989, 30(34):4493–4496.

Seel and Vogtle, "Molecular Recognition and Transport of Nucleobases—Superiority of Macrobicyclid Host Molecules," *Angew, Chem. Int. Ed. Engl.*, 1991, 30(4):442–444.

Sessler et al., "Anion Binding: A New Direction In Porphyrin–Related Research," *Pure & Applied Chem.*, 65(3):393–398, 1993.

Sessler et al., "Cytosine Amine Derivatives," *J. Org. Chem.*, 1992, 47:826–834.

Aoyama et al., "Multi–Point Interaction of Phosphates with Protonated Pyridylporphyrin. Discrimination of Monoalkyl and Dialkyl Phosphates," *Chemistry Letters*, 1241–1244 (1991).

Claude et al., "Binding of Nucleosides, Nucleotides and Anionic Planar Substrates by Bis–Intercaland Receptor Molecules," *J. Chem. Soc. Chem. Commun.*, 1991, 17:1182–1185.

Cramer et al., "Synthesis and Structure of the Chloride and Nitrate Inclusion Complexes of [16–Pyrimidinium crown–4]," *J. Am. Chem. Soc.*, 1991, 113:7033–7034.

Tabushi et al., "Lipophilic Diammonium Cation Having a Rigid Structure Complementary to Pyrophosphate Dianions of Nucleotides. Selective Extraction and Transport of Nucleotides," *J. Am. Chem. Soc.*, 1981, 103:6152–6157.

Tohda et al., "Liquid Membrane Electrode for Guanosine Nucleotides Using a Cytosine–Pendant Triamine Host as the Sensory Element," *Analytical Chemistry*, 1992, 64(8):960–964.

Sessler et al., "Gadolinium (III) Texaphyrin: A Novel MRI Contrast Agent," *Journal of the American Chemical Society*, 115(22):10,368–10,369,1993.

Ehrenberg et al., "Spectroscopy, Photokinetics and Cellular Effect of Far–Red and Near Infrared Absorbing Photosensitizers," *Proc. SPIE–Int. Soc. Opt. Eng 1992, 1645 (Proc. Opt. Methods Tumor Treat. Dect.: Mech. Tech. Photodyn. Ther.*, 259–263, 1992.

Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Goodchild, John, "Conjugates of Oligonucleotides and Modified Oligonucleotides: A Review of Their Synthesis and Properties," *Bioconjugate Chemistry*, 1(3):165–187, 1990.

Kobayashi et al., "Uptake of Chlorophyll–Derivatives by Cellular Nuclei and Mitochondria," *Photomed. Photobiol.*, 15:75–84, 1993.

Brown and Truscott, "New Light on Cancer Therapy," *Chemistry in Britain*, 955–958, 1993.

Lin et al., "Use of EDTA Derivatization to Characterize Interactions between Oligodeoxyribonucleoside Methylphosphonates and Nucleic Acids," *Biochemistry*, 28:1054–1061, 1989.

Strobel and Dervan, "Cooperative Site Specific Binding of Oligonucleotides to Duplex DNA," *Journal of the American Chemical Society*, 111(18):7286–7287, 1989.

Doan et al., "Sequence–targeted Chemical Modifications of Nucleic Acids by Complementary Oligonucleotides Covalently Linked to Porphyrins," *Nucleic Acids Research*, 15(21):8643–8659, 1987.

Doan et al., "Targeted Cleavage of Polynucleotides by Complementary Oligonucleotides Covalently Linked to Iron–Prophyrins," *Biochemistry*, 26:6736–6739, 1986.

Dervan, Peter B., "Design of Sequence–Specific DNA–Binding Molecules," *Science*, 232:464–471, 1986.

Groves and Farrell, "DNA Cleavage by a Metal Chelating Tricationic Porphyrin," *J. Am. Chem. Soc.*, 111:4998–5000, 1989.

Zuk et al., "Pharmacokinetic and Tissue Distribution Studies of the Photosensitizer bis(Di–Isobutyl Octadecysiloxy)Silicon 2,3–Naphthalocyanine (isoBosinc) in Normal and Tumor–Bearing Rats," *Photochemistry and Photobiology*, 59(1):66–72, 1994.

Lee et al., "Interaction of Psoralen–Derivatized Oligodeoxyribonucleoside Methylphosphonates with Single–Stranded DNA," *Biochemistry*, 27:3197–3203, 1988.

Bhan and Miller, "Photo–Cross Linking of Psoralen–Derivatized Oligonucleoside Methylphosphonates to Single–Stranded DNA," *Bioconjugate Chem.*, 1:82–88, 1990.

Boutorine et al., "Fullerene–Oligonucleotide Conjugates: Photo–Induced Sequence Specific DNA Cleavage", *Agnew. Chem. Int. Ed. Engl.*, 33(23/24):2462–2465, 1994.

Dolphin et al., "Porphocyanine: An Expanded Tetrapyrrolic Macrocycle," *J. Am. Chem. Soc.,* 115:9301–9302, 1993.

Ehrenberg et al., "The Binding and Photosensitization Effects of Tetrabenzoporphyrins and Texaphyrin in Bacterial Cells," *Lasers in Medical Science*, 8:197–203, 1993.

Le Doan et al., "Sequence–Targeted Photochemical Modifications of Nucleic Acids by Complementary Oligonucleotides Covalently Linked to Porphyrins," *Bioconjugate Chem.,* 1:108–113, 1990.

Le Doan et al., "Sequence–Specific Recognition, Photocrosslinking and Cleavage of the DNA Double Helix by an Oligo–[α]–Thymidylate Covalently Attached to an Azidoproflavine," *Nucleic Acids Res.*, 15:7749–7760, 1987.

Levina et al., "Photomodification of RNA and DNA Fragments by Oligonucleotide Reagents Bearing Arylazide Groups," *Biochimie*, 75:25–27, 1993.

Mastruzzo et al., "Targeted Photochemical Modification of HIV–Derived Oligoribonucleotides by Antisense Oligodeoxynucleotides Linked to Porphyrins," *Photochem. Photobiol.*, 60(4):316–322, 1994.

Fedorova et al., "Palladium(II)–Coproporphyrin I as a Photoactivable Group in Sequence–Specific Modification of Nucleic Acids by Oligonucleotide Derivatives," *FEBS Lett.*, 259(2):335–337, 1990.

Morgan and Skalkos, "Second Generation Sensitizers: Where are We and Where Should We Be Going?" *Proc. SPIE Int. Soc. Opt. Eng. Ser.*, 6:87–106, 1990

Perrouault et al., "Sequence–Specific Artificial Photo–Induced Endonucleases Based on Triple Helix–Forming Oligonucleotides," *Nature*, 344:358–360, 1990.

Pieles and Englisch, "Psoralen Covalently Linked to Oligodeoxyribonucleotides: Synthesis, Sequence Specific Recognition of DNA and Photo–Cross–Linking to Pyrimidine Residues of DNA," *Nucleic Acids Res.,* 17(1):285–299, 1989.

Praseuth et al., "Sequence–Targeted Photosensitized Reactions in Nucleic Acids by Oligo–α–Deoxynucleotides and Oligo–β–Deoxynucleotides Covalently Linked to Proflavin," *Biochemistry*, 27:3031–3038, 1988.

Praseuth et al., "Sequence–Specific Binding and Photocrosslinking of α and β Oligodeoxynucleotides to the Major Groove of DNA via Triple–Helix Formation," *Proc. Natl. Acad. Sci. USA*, 85:1349–1353, 1988.

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Natl. Acad. Sci. USA*, 88:5602–5606, 1991.

Teare and Wollenzien, "Specificity of Site Directed Psoralen Addition to RNA," *Nucleic Acids Res.*, 17(9):3359–3372, 1989.

Vogel et al., "New Porphycene Ligands: Octaethyl–and Etioporphycene (OEPc and EtioPc)–Tetra–and Pentacoordinated Zinc Complexes of OEPc," *Angew. Chem. Int. Ed. Engl.*, 32(11):1600–1604, 1993.

Wessel et al., "Porphyrins with Aromatic 26π–Electron Systems," *Agnew. Chem. Int. Ed. Eng.*, 32(8):1148–1151, 1993.

Agrawal et al., "Cellular Uptake and Anti–HIV Activity of Oligonucleotides and Their Analogs," *Gene Regulation: Biology of Antisense RNA and DNA*, 273–283, 1992.

Agrawal and Tang, "Efficient Synthesis of Oligoribonucleotide and Its Phosphorothioate Analogue Using H–Phosphonate Approach," *Tetrahedron Letters*, 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Basile et al., "Metal–Activated Hydrolytic Cleavage of DNA," *J. Am. Chem. Soc.*, 109:7550–7551, 1987.

Bradley et al., "Antisense Therapeutics," *Gene Regulation: Biology of Antisense RNA and DNA*, 285–293, 1992.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13):4951–4958, 1992.

Chin and Banaszczyk, "Rate–Determining Complexation in Catalytic Hydrolysis of Unactivated Esters in Neutral Water," *J. Am. Chem. Soc.*, 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.*, 111:4103–4105, 1989.

Chin et al., "Co(III) Complex Promoted Hydrolysis of Phosphate Diesters: Comparison in Reactivity of Rigid cis–Diaquotetraazacobalt(III) Complexes," *J. Am. Chem. Soc.*, 111:186–190, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," Tetrahedron Letters, 31(38):5413–5416, 1990.

Furuta et al., "Phosphate Anion Binding: Enhanced Transport of Nucleotide Monophosphates Using a Sapphyrin Carrier," *J. Am. Chem. Soc.*, 113:6677–6678, 1991.

Hanvey et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am. Chem. Soc.*, 111:2521–2527, 1989.

Kim and Chin, "Dimethyl Phosphate Hydrolysis at Neutral pH," *J. Am. Chem. Soc.*, 114:9792–9795, 1992.

Komiyama et al., "Unprecedentedly Fast Hydrolysis of the RNA Dinucleoside Monophosphates ApA and UpU by Rare Earth Metal Ions," *J. Chem. Soc. Chem. Commun.*, 640–641, 1992.

Menger et al., "Phosphate Ester Hydrolysis Catalyzed by Metallomicelles," *J. Am. Chem. Soc.*, 109:2800–2803, 1987.

Modak et al., "Toward Chemical Ribonucleases. 2. Synthesis and Characterization of Nucleoside–Bipyridine Conjugates. Hydrolytic Cleavage of RNA by Their Copper(II) Complexes," *J. Am. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications," *J. Am. Chem. Soc.*, 114:1903–1905, 1992.

Ranganathan et al., "Design of a Chemical Nuclease Model with $(Lys)_2Cu$ as the Core Motif," *Journal of the Chemical Society*, 4:337–339, 1993.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remarkably Fast Hydrolysis of 3',5'-= Cyclic Adenosine Monophosphate by Cerium(III) Hydroxide Cluster," *J. Chem. Soc. Chem. Comm.*, 2 pages, 1992.

To and Neiman, "The Potential For Effective Antisense Inhibition of Retroviral Replication Mediated by Retroviral Vectors," *Gene Regulation: Biology of Antisense RNA and DNA*, 261–271, 1992.

Shelton and Morrow, "Catalytic Transesterification and Hydrolysis of RNA by Zinc(II) Complexes," *Inorg. Chem.*, 30:4295–4299, 1991.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Kolasa et al., "Trivalent Lanthanide Ions Do Not Cleave RNA in DNA–RNA Hybrids", *Inorg. Chem.*, 32:3983–3984, 1993.

Schneider et al., "Catalysis of the Hydrolysis of Phosphoric Acid Diesters by Lanthanide Ions and the Influence of Ligands," *Angew. Chem. Int. Ed. Engl.*, 32(12):1716–1719, 1993.

Hayashi et al., "Site-Selective Hydrolysis of tRNA by Lanthanide Metal Complexes," *Inorg. Chem.*, 32:5899–5900, 1993.

Magda et al., "Sequence–Specific Photocleavage of DNA by an Expanded Porphyrin with Irradiation Above 700 nm," *J. Am. Chem. Soc.*, 117:3629–3630, 1995.

U.S. Serial No. 08/075,123 to Sessler et al. filed Jun. 9, 1993.

U.S. Serial No. 08/098,514 to Sessler et al. filed Jul. 28, 1993.

U.S. Serial No. 08/112,786 to Sessler et al. filed Aug. 25, 1993.

U.S. Serial No. 08/135,118 to Sessler et al. filed Oct. 12, 1993.

U.S. Serial No. 08/302,061 to Sessler et al. filed Sep. 7, 1994.

U.S. Serial No. 08/280,351 to Sessler et al. filed Jul. 26, 1994.

U.S. Serial No. 08/196,964 to Sessler et al. filed Feb. 15, 1994.

U.S. Serial No. 08/227,370 to Sessler et al. filed Apr. 14, 1994.

U.S. Serial No. 08/207,845 to Sessler et al. filed Mar. 8, 1994.

U.S. Serial No. 08/452,261 to Sessler et al. filed May 26, 1995.

U.S. Serial No. 08/236,218 to Sessler et al. filed Apr. 28, 1994.

U.S. Serial No. 08/310,501 to Sessler et al. filed Sep. 21, 1994.

U.S. Serial No. 08/437,968 to Sessler et al. filed May 10, 1995.

U.S. Serial No. 08/433,573 to Sessler et al. filed May 3, 1995.

U.S. Serial No. 08/449,417 to Sessler et al. filed May 24, 1995.

U.S. Serial No. 08/458,909 to Sessler et al. filed Jun. 2, 1995.

U.S. Serial No. 08/449,681 to Sessler et al. filed May 24, 1995.

U.S. Serial No. 08/484,551 to Sessler et al. filed Jun. 7, 1995.

U.S. Serial No. 08/458,347 to Sessler et al. filed Jun. 2, 1995.

U.S. Serial No. 08/459,333 to Sessler et al. filed Jun. 2, 1995.

U.S. Serial No. 08/485,581 to Magda et al. filed Jun. 7, 1995.

U.S. Serial No. 08/486,962 to Magda et al. filed Jun. 7, 1995.

U.S. Serial No. 08/486,886 to Hemmi et al. filed Jun. 7, 1995.

U.S. Serial No. 08/486,935 to Hemmi et al. filed Jun. 6, 1995.

U.S. Serial No. 08/486,209 to Hemmi et al. filed Jun. 6, 1995.

U.S. Serial No. 08/469,177 to Magda et al. filed Jun. 6, 1995.

U.S. Serial No. 08/486,967 to Sessler et al. filed Jun. 7, 1995.

U.S. Serial No. 08/486,311 to Magda et al. filed Jun. 7, 1995.

U.S. Serial No. 08/487,722 to Magda et al. filed Jun. 7, 1995.

Stein et al. "Antisense Oligonucleotides as Therapeutic Agents—Is the Bullet Really Magical?" Science, vol. 261, p. 1004, Aug. 1993.

Uhlmann et al. "Antisense Oligonucleotides: A new Therapeutic Principle" Chemical Reviews, vol. 90, p. 543, Jun. 1990.

Morrow "Hydrolytic cleavage of RNA catalyzed by metal ion complexes" Metal Ions in Biological Systems, vol. 33, pp. 561–592, 1996.

$EuTx-NH(CH_2)_6-HN$ 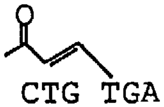
CAT CTG TGA GCC GGG TGT TG — $9_A$ SEQ. ID. NO. 2

$EuTxNH(CH_2)_6-PO_4-$CAT CTG TGA GCC GGG TGT TG — $9_B$ SEQ. ID. NO. 2

$EuTx-NH(CH_2)_6-HN$ 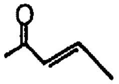
CTC GGC CAT AGC GAA TGT TC — $9_C$ SEQ. ID. NO. 1

$EuTxNH-(CH_2)_6-PO_4-$CTC GGC CAT AGC GAA TGT TC — $9_D(10_A)$ SEQ. ID. NO. 1

$N_2H-(CH_2)_6-PO_4-$CTC GGC CAT AGC GAA TGT TC — $9_E$ SEQ. ID. NO. 1

$DyTxNH-(CH_2)_6-PO_4-$CTC GGC CAT — $9_F$ SEQ. ID. NO. 6

$DyTxNH-(CH_2)_6-PO_4-$CTC GGC CAT AGC — $9_G$ SEQ. ID. NO. 5

$DyTxNH-(CH_2)_6-PO_4-$CTC GGC CAT AGC GAA TGT TC — $9_H$ SEQ. ID. NO. 1

$DyTxNH-(CH_2)_6-PO_4-$CTC CTG TGA GCC GGG TGT TG — $9_I(10_C)$ SEQ. ID. NO. 2

CTC GGC CAT AGC$-PO_4-CH_2CHOHCH_2-NHEuTx$ — $9_J$ SEQ. ID. NO. 5

CTC GGC CAT AGC$-PO_4-CH_2CH(CH_2OH)(CH_2)_4-NHEuTx$ — $9_K$ SEQ. ID. NO. 5

$EuTxHN-(CH_2)_6-PO_4-$CTC GGC CAT AGC$-PO_4-CH_2CH(CH_2OH)(CH_2)_4-NHEuTx$ — $9_L$ SEQ. ID. NO. 5

$EuTxHN-(CH_2)_6-PO_4-$TAG CGA ATG TTC — $9_M$ SEQ. ID. NO. 10

CTC GGC CAT AGC$-PO_4-CH_2CH(CH_2OH)(CH_2)_4-NHLuTx$ — $9_N$ SEQ. ID. NO. 5

$LuTxHN-(CH_2)_6-PO_4-$CTC GGC CAT AGC — $9_O$ SEQ. ID. NO. 5

FIG. 2

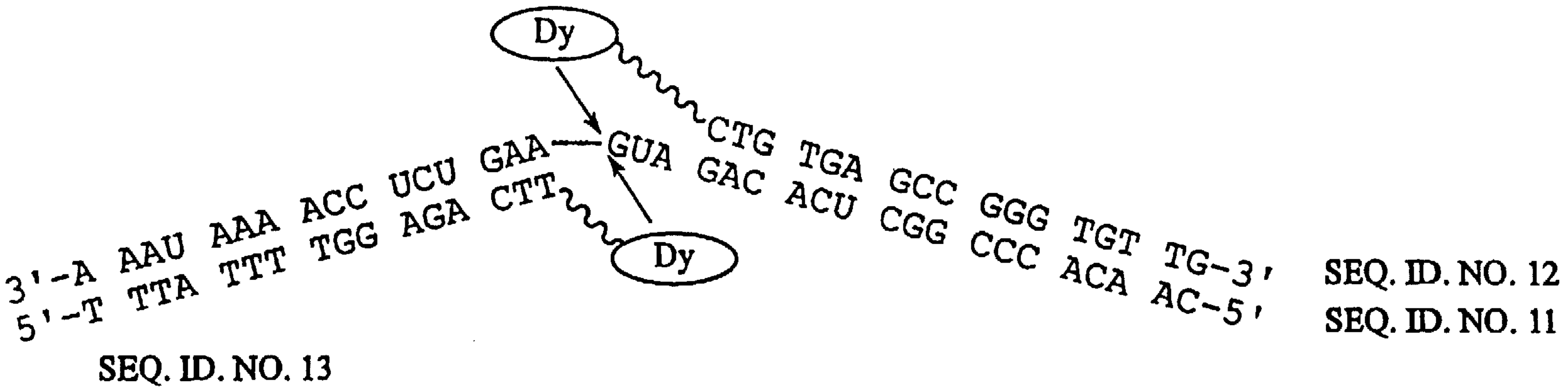

5'-DyTxNH-$(CH_2)_6$-$PO_4$-TG TGA GCC GGG TGT TG-3' SEQ. ID. NO. 14

5'-DyTxNH-$(CH_2)_6$-$PO_4$-CTG TGA GCC GGG TGT TG-3' SEQ. ID. NO. 12

5'-DyTxNH-$(CH_2)_6$-$PO_4$-T CTG TGA GCC GGG TGT TG-3' SEQ. ID. NO. 15

5'-DyTxNH-$(CH_2)_6$-$PO_4$-AT CTG TGA GCC GGG TGT TG-3' SEQ. ID. NO. 16

5'-DyTxNH-$(CH_2)_6$-$PO_4$-CAT CTG TGA GCC GGG TGT TG-3' SEQ. ID. NO. 2

3'-A AAU AAA ACC UCU GAA GUA GAC ACU CGG CCC ACA AC-5' SEQ. ID. NO. 11

5'-T TTA TTT TGG AGA CTT-$PO_4$-$CH_2CHOHCH_2$-NHDyTx-3' SEQ. ID. NO. 13

5'-T TTA TTT TGG AGA CTT-$PO_4$-$CH_2CH(CH_2OH)(CH_2)_4$-NHDyTx-3' SEQ. ID. NO. 13

FIG. 5

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:1:

CTCGGCCATA GCGAATGTTC 20

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:2:

CTCCTGTGAG CCGGGTGTTG 20

( 2 ) INFORMATION FOR SEQ ID NO:3:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "RNA"

( x i ) SEQUENCE DESCRIPTION: SEQ ID NO:3:

CACUGUAGAA GAGCCGGUAU CGCUUACAAG 30

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:4:

CATCTGTGAG CCGGGTGTTG 20

-continued ( 2 ) INFORMATION FOR SEQ ID NO:5:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:5:

CTCGGCCATA GC 12

( 2 ) INFORMATION FOR SEQ ID NO:6:

( i ) SEQUENCE CHARACTERISTICS:
( A ) LENGTH: 9 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:6:

CTCGGCCAT 9

( 2 ) INFORMATION FOR SEQ ID NO:7:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:7:

ATAGCGATGT TC 12

( 2 ) INFORMATION FOR SEQ ID NO:8:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "RNA"

( x i ) SEQUENCE DESCRIPTION: SEQ ID NO:8:

CACUGUAGAA GAGCCGGUAU CGCUACAAG 29

( 2 ) INFORMATION FOR SEQ ID NO:9:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:9:

ATAGCGATGT 10

-continued ( 2 ) INFORMATION FOR SEQ ID NO:10:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:10:

TAGCGAATGT TC 12

( 2 ) INFORMATION FOR SEQ ID NO:11:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "RNA"

( x i ) SEQUENCE DESCRIPTION: SEQ ID NO:11:

AAAUAAAACC UCUGAAGUAG ACACUCGGCC CACAAC 36

( 2 ) INFORMATION FOR SEQ ID NO:12:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:12:

CTGTGAGCCG GGTGTTG 17

( 2 ) INFORMATION FOR SEQ ID NO:13:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:13:

TTTATTTTGG AGACTT 16

( 2 ) INFORMATION FOR SEQ ID NO:14:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:14:

TGTGAGCCGG GTGTTG 16

-continued ( 2 ) INFORMATION FOR SEQ ID NO:15:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:15:

TCTGTGAGCC GGGTGTTG 18

( 2 ) INFORMATION FOR SEQ ID NO:16:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:16:

ATCTGTGAGC CGGGTGTTG 19

( 2 ) INFORMATION FOR SEQ ID NO:17:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:17:

GAGGCTGCTG GTTTT 15

( 2 ) INFORMATION FOR SEQ ID NO:18:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:18:

CATCTGTGAG CCGGG 15

METHOD OF PHOSPHATE ESTER HYDROLYSIS

This application is a continuation of co-pending application U.S. Ser. No. 08/485,581, filed Jun. 7, 1995 now abandoned, which is a continuation-in-part of application U.S. Ser. No. 08/452,261, filed May 26, 1995 now abandoned, which is a continuation of International application No. PCT/US94/06284 designating the United States, filed Jun. 9, 1994, which is a continuation-in-part of application U.S. Ser. No. 08/227,370, filed Apr. 14, 1994, now U.S. Pat. No. 5,559,207, which is a continuation-in-part of application U.S. Ser. No. 08/075,123, filed Jun. 6, 1993, now abandoned which is a continuation-in-part of application U.S. Ser. No. 07/822,964, filed Jan. 1, 1992 now U.S. Pat. No. 5,252,720.

The government has certain rights in the present invention pursuant to National Institutes of Health, National Cancer Institute SBIR Grant No. 1 R43 CA67728-01.

FIELD OF THE INVENTION

The present invention relates to catalysts for the cleavage of ester bonds, and particularly phosphate ester bonds, including those related to a biological system.

BACKGROUND OF THE INVENTION

Many divalent and trivalent metal salts have been shown to promote the hydrolysis of phosphate ester bonds. Komiyama et al. (1992) reported the hydrolysis of adenylyl (3'-5')adenosine and uridyl(3'-5')uridine at pH 8.0, 30° C. by rare earth metal(III) ions. A cerium(III) hydroxide cluster has been reported to hydrolyze 3',5'-cyclic adenosine monophosphate (Sumaoka, et al. 1992). Browne and Bruice (1992) reported the hydrolysis of bis(8-hydroxyquinoline) phosphate in the presence of divalent cations. However, in order to convey a degree of specificity to catalysis by the metal ion, complexes of metals with various ligands have been studied. The ligand may serve a number of roles in catalysis, including modulation of catalytic efficiency and maintenance of the metal ion in solution, while also allowing for coupling of reagents having a binding specificity for a desired substrate.

Ligands complexing metal ions for use in the hydrolysis of phosphate ester bonds include: tris(aminopropyl)amine (trpn), 1,4,7,10-tetraazacyclododecane (cyclen), tris(2-aminoethyl)amine (tren), triethylenetetramine (trien), tetraethylenepentamine (tetren), bipyridine conjugates, imidazole, cyclodextrin derivatives, lysine, terpyridine (trpy), 1,2-diaminoethane, a bis(diaquo) complex, "metallomicelles" and a phenanthrolinepolyamine tridentate complex (Basile et al. 1987; Menger et al. 1987; Chung et al. 1990; Hendry and Sargeson, 1989; Shelton and Morrow, 1991; Ranganathan et al. 1993; Breslow and Huang, 1991; Modak et al. 1991; Kim and Chin, 1992; Chin et al. 1989; Chin and Banaszczyk, 1989a,b; Chin and Zou, 1987).

In order for a metal complex to function catalytically in vivo, the complex should not release bound metal ion. Morrow et al. (1992) have studied the cleavage of RNA by a lanthanide(III) hexamine Schiff-base (HAM) macrocyclic complex. Cleavage of the dinucleotide adenylyl-3',5'uridine 3'-monophosphate (ApUp) or of oligomers of adenylic acid (A12-A18) was reported at 37° C. after 4 hours by several lanthanide complexes. Other hexadentate ligands such as EDTA formed lanthanide(III) complexes that were completely inactive in RNA cleavage under similar conditions. Inertness of the macrocyclic complex to metal release was reported to change dramatically throughout the lanthanide series. These complexes have some serious disadvantages, including high toxicity of the HAM ligand, weak coordination and dissociation of the lanthanide metals. Further, the ligand cannot be easily modified which precludes the generation of derivatives with substrate specificity.

Given the limitations of the HAM complex, it is clear that the development of new macrocycles capable of chelating lanthanide metals and forming stable complexes which are able to cleave RNA would be of utility.

Texaphyrins are aromatic pentadentate macrocyclic "expanded porphyrins" which have been found to be useful as MRI contrast agents, as radiation sensitizers and in photodynamic therapy (PDT). Texaphyrin is considered as being an aromatic benzannulene containing 22$\pi$-electron delocalization pathways. See, e.g., Sessler, J. L. et al., *Accounts of Chemical Research,* 1994, 27:43. Texaphyrins and water-soluble texaphyrins and methods of preparation have been described in U.S. Pat. Nos. 4,935,498; 5,252,720; 5,256,399; 5,272,142; and 5,292,414; and in International application Ser. No. PCT/US95/01996; all of which are incorporated herein by reference.

Antisense therapeutics are designed to bind to complementary RNA targets by mimicking the DNA template used in their production. Complexation to an RNA target, itself, is usually insufficient to inhibit protein synthesis by the RNA, as cellular factors such as ribosomes compete effectively for the RNA. Nonetheless, the desired biological effect has often been observed due to the activity of the enzyme RNase H. This enzyme catalyzes the degradation of RNA present as a heteroduplex (RNA that is bound by single-stranded DNA or by an oligonucleotide-based therapeutic which is sufficiently similar in structure to DNA). Although operative in many cells, this mechanism has the drawback that it relies on participation of an enzyme to activate the RNA-oligonucleotide heteroduplexes. Also, as RNase H is a nuclear enzyme, this mechanism of action is presumably confined to this cellular compartment.

An important consideration in the development of antisense agents is their delivery to the target cells and the genetic material. Due to the presence of enzymes which degrade them, RNA and DNA are not sufficiently stable to be administered in their native forms. Limited penetration of these charged oligomeric materials into cells or nuclei also presents a serious challenge to this approach. For these reasons, a large number of structural analogs, such as the phosphorothioates and 2'-O-methyl RNA, have been investigated as antisense agents. Whereas such analogs often overcome the problems of instability or poor cellular uptake, the chemical modifications usually eliminate the ability of the antisense agent to elicit RNase H activity. Phosphorothioate analogs are noteworthy in that they display high stability and retain substrate activity for RNase H. The phosphorothioates are currently being evaluated in Phase III clinical trials for treatment of cytomegalovirus retinitis in AIDS patients. However, because they rely on the RNase H enzyme for their activity, little or no structural modifications can be made to these analogs, thus limiting their versatility.

Another approach to antisense therapy is based on the application of ribozyme chemistry. Ribozymes are enzymes made of RNA that are able to hydrolytically cleave complementary RNA substrates in a catalytic fashion. Originally discovered as sequences of RNA that catalyze their own removal during nuclear processing, modified forms of these enzymes are being developed as antisense agents. These tailored ribozymes cannot be administered as therapeutics, however, due to their size and structure and the inherent instability of RNA.

In view of the limitations of the natural ribozyme and oligonucleotide analog-based antisense approaches, it would be desirable to develop a therapeutic exhibiting nuclease stability, strength of hybridization and cell penetrability without regard for its ability to act as a substrate for endogenous RNase H.

SUMMARY OF THE INVENTION

The present invention seeks to solve the problems found in the prior art by providing metallotexaphyrin complexes and metallotexaphyrin complex-conjugates for phosphate ester hydrolysis that provide stable complexation for an otherwise toxic metallic cation, specificity for targeted sites in a therapeutic application, and sufficient nontoxicity for in vivo use.

The present invention involves the discovery that metallotexaphyrin complexes catalyze the hydrolysis of phosphate ester linkages. Texaphyrins are unique molecules in that they complex the metal in a very stable molecule but allow access to the metal coordination sites, thus preserving the metal's reactivity and its ability to hydrolyze phosphoester bonds. Furthermore, the texaphyrin molecule allows for derivatization for various biological applications. The texaphyrin complex is far less toxic and far more stable than the HAM complex as well.

Thus, the present invention provides a method of phosphate ester hydrolysis. The method comprises contacting a phosphate ester, in aqueous solution, with a metallotexaphyrin complex having catalytic activity for phosphate ester bond hydrolysis, the contact being under conditions and for a time sufficient to hydrolyze the phosphate ester.

A metallotexaphyrin complex as used herein is an aromatic pentadentate expanded porphyrin analog metal complex with appended functional groups. Such pendant groups may enhance solubility or biolocalization or may provide coupling sites for site-directed molecules or catalytic groups.

It will be apparent to one of skill in the art in light of the present disclosure that a variety of phosphate ester linkages may be cleaved by the molecules of the present invention. Exemplary ester linkages cleaved by the molecules of the present invention include phosphate monoester and diester linkages, especially physiologically important phosphate linkages present in nucleic acids such as RNA; p-nitrophenylphosphate ester, a widely used substrate for assays; phosphoric anhydrides, including important mediators of metabolism such as nucleotides ATP, ADP, AMP, cAMP, UDP, NADH, NADPH, FAD or $FADH_2$, for example; and phospholipids such as phosphatidyl choline and sphingomyelin that are important in nerve and brain functions.

Metallotexaphyrin complexes possess inherent biolocalization. Additionally, in one embodiment of the present invention, the metallotexaphyrin complexes are further coupled to site-directed molecules to form conjugates for targeted in vivo delivery. "Specificity for targeted sites" means that upon contacting the metallotexaphyrin complex-conjugate with the targeted site, for example under physiological conditions of ionic strength, temperature, pH and the like, specific binding will occur. The interaction may occur due to specific electrostatic, hydrophobic, entropic or other interaction of certain residues of the conjugate with specific nucleotide, amino acid or glycolytic residues of the target to form a stable complex under the conditions effective to promote the interaction. In the present invention, this interaction will allow cleavage of an ester linkage that is in the vicinity of the specific binding.

Another embodiment of the present invention is a method of phosphate ester hydrolysis comprising contacting a phosphate ester, in aqueous solution, with a metallotexaphyrin complex linked to a sapphyrin. Sapphyrins have binding specificity for phosphate esters. The contact is under conditions and for a time sufficient to hydrolyze the phosphate ester.

Another embodiment of the present invention is a method for targeted intracellular RNA hydrolysis. The method comprises the introduction into a cell of a metallotexaphyrin complex coupled to an oligonucleotide having complementary binding affinity for a targeted RNA, whereby hydrolysis of the targeted RNA is catalyzed by the metallotexaphyrin complex. The RNA may be, for example, viral RNA (including retroviral RNA), messenger RNA (mRNA), ribosomal RNA, RNA cofactors, transfer RNA, small nuclear RNA, and small cytoplasmic RNA, thereby providing a multifactorial approach to eliminating diseased, cancerous or other unwanted cells or tissues. A site of desired hydrolysis may be a position novel to undesired organisms in terms of health care. A site of desired hydrolysis may be an mRNA encoding a product deleterious to the host or may be a normal mRNA that is deleterious in some way. The mRNA may be transcribed from an oncogene or it may encode a growth factor, for example.

Texaphyrins are ideal for intracellular transport and cell delivery of a large variety of monomeric and oligomeric nucleotide species and their derivatives, including RNA, DNA, anti-viral agents and antisense agents. Texaphyrins exhibit the ability to cross cellular membranes. When the texaphyrin is complexed or conjugated to a second molecule, the second molecule, in the present case an oligonucleotide, will be transported across the membrane and into the cell together with the texaphyrin.

A further embodiment of the invention is a method of modulating the activity of an RNA, comprising contacting the RNA with a metallotexaphyrin complex either directly or in cells, tissues or bodily fluids containing the RNA, under conditions and for a time sufficient to hydrolyze the RNA. The metallotexaphyrin complex is selected from those that exhibit catalytic activity for RNA hydrolysis, and the complex is present in an amount effective to modulate the RNA activity or function. By "modulating the activity of an RNA" is meant that the metallotexaphyrin complex interferes with or otherwise diminishes the RNA activity or function. A preferred function to be modulated is the export of mRNA from cell nuclei. Another is splicing of the mRNA. Yet another function is translation of the mRNA into a protein, thereby modulating the production of a protein by an organism. Generally, the mRNA selected is cell-, tissue- or disease-specific. In a presently preferred embodiment, the metallotexaphyrin complex is coupled to an oligonucleotide having complementary binding affinity for the RNA whose activity is to be modulated.

A method for inhibiting the expression of a gene in an animal comprising the administration to the animal of a metallotexaphyrin complex-oligonucleotide conjugate is a further embodiment of the present invention. The oligonucleotide may have complementary binding affinity for messenger RNA transcribed from said gene or may be complementary to either strand of the DNA surrounding the gene or encoding the gene. The gene may be an oncogene or it may encode a growth factor, for example. A further embodiment of the present invention is a method for inhibiting the expression of a gene in a particular tissue of an animal comprising administering to the animal a metallotexaphyrin-oligonucleotide conjugate having specificity for the tissue. The metallotexaphyrin complex-conjugate may have appended an oligonucleotide complementary to the target gene and a further appended tissue-specific molecule like estradiol, for example, or an antibody directed for said tissue or a peptide having affinity for a biological receptor on said tissue.

A further embodiment of the present invention is a texaphyrin metal complex-conjugate wherein two or more separate metallotexaphyrin complexes are attached to an oligonucleotide, one at the 3' and one at the 5' end, and/or one or more at an internal residue, and/or two complexes at one end, e.g. a "dimer" of two metallotexaphyrins at the 5' end of the oligonucleotide. The metal ion of each of the texaphyrin complexes may be the same or it may be different. Use of a dual metallotexaphyrin complex-conjugate should effect the hydrolysis of RNA with increased efficiency due to the concerted activity of the metal complexes. For diagnosis and treatment purposes, the administration of such a conjugate with one texaphyrin complex having an ester bond-hydrolyzing metal species and the other having a paramagnetic species would allow binding, imaging and hydrolysis, all effected by one conjugate. In this case, binding is effected by the oligonucleotide, imaging is accomplished by MRI due to the presence of the paramagnetic metal ion and hydrolysis is accomplished by the ester bond-hydrolyzing metal species. Therefore, the biodistribution and cellular penetration of the conjugate may be determined.

BRIEF DESCRIPTION OF THE DRAWINGS

FIG. 2 shows europium(III) texaphyrin (EuTx) DNA conjugates of Example 3, dysprosium(III) texaphyrin (DyTx) conjugates of Example 4, oligonucleotides conjugated at the 3' end to texaphyrin, and dual conjugates, i.e., oligonucleotides having a texaphyrin conjugated to the 5' and to the 3' ends. Oligonucleotides are written in a 5'→3' direction.

FIG. 5 shows the use of a set of metallotexaphyrin complex-oligonucleotide conjugates targeted for the same hydrolysis site on the RNA template.

FIG. 6 is a comparison of a sequence-specific DyTx-oligonucleotide conjugate with its non-conjugated oligonucleotide analog. FIG. 7 is a comparison of the sequence-specific DyTx-oligonucleotide conjugate with a sequence-nonspecific DyTx-oligonucleotide conjugate.

DETAILED DESCRIPTION OF THE PREFERRED EMBODIMENTS

Figure 1:
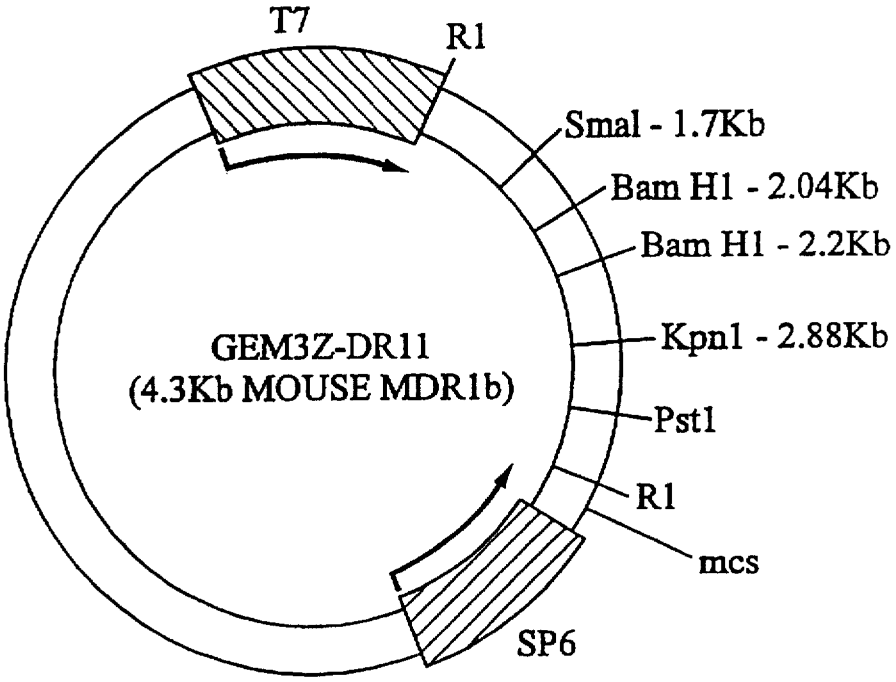
FIG. 1 shows the recombinant plasmid from which $^{32}P$-labelled 2000 base pair RNA transcripts were made for the RNA hydrolysis experiments of Example 2. R1=EcoRI, MCS=multi-cloning sequence.

The present invention involves the use of metallotexaphyrin complexes for the hydrolytic cleavage of ester bonds. More particularly, the invention involves the cleavage of phosphate ester bonds of a diester, a monoester, an RNA substrate, and the like, using a metal complex of a texaphyrin.

The texaphyrins have now been shown by the inventors to catalyze the hydrolysis of phosphate ester bonds. More specifically, a metallotexaphyrin complex or a metallotexaphyrin complex-conjugate having catalytic activity for ester bond hydrolysis is added to an aqueous solution containing a phosphate ester and is incubated for a time and under conditions sufficient to hydrolyze the phosphate ester bond. Such conditions are known to those of skill in the art or can be determined by such persons without undue experimentation. It has been found that such conditions include physiologic conditions. This is especially useful when the texaphyrin complexes are used in vivo as a treatment procedure to hydrolyze RNA, for example.

The phosphate ester can be contacted with the metallotexaphyrin complex or complex-oligonucleotide conjugate either directly, such as would be the case in certain diagnostic applications, or in cells, tissues or bodily fluids containing the phosphate ester.

Potential particular applications for the process of this invention include the specific cleavage and possible subsequent recombination of RNA; destruction of viral or bacterial RNA; digestion of cell membrane components such as phosphatidyl cholines and sphingomyelin; disruption of the transfer of free energy in cells by hydrolyzing ATP, ADP, NADH, NADPH, FAD or $FADH_2$; treatment of liver diseases by preventing the formation of glycogen; regulation of hormones by hydrolysis of cAMP; hydrolysis of mutagenic and carcinogenic di- and trialkyl phosphates commonly used as solvents; and the detoxification of phosphate ester nerve gases and insecticides by hydrolysis of phosphate ester bonds. In a presently preferred embodiment, the phosphate ester is a nucleic acid ester.

The aqueous phosphate ester solution may be a solution or a suspension of nucleic acid, for example, a solution or suspension of RNA or DNA. The aqueous phosphate ester solution may be the intracellular environment containing the target RNA or DNA, or it may be or bodily fluids. The aqueous solution may, in addition, be water from a stream, river or lake, for example, or effluent that contains a physiologically or environmentally undesirable phosphate ester-containing compound. RNA is more preferably hydrolyzed than DNA by a factor of about $10^{12}$. When the phosphate ester is RNA, the metal is preferably a lanthanide or a lanthanoid metal cation, more preferably Tb(III) or Dy(III).

In the practice of the present invention, the texaphyrin macrocycle to be complexed to the metal ion may be chosen from any texaphyrin molecule, including those now known and disclosed in the U.S. patents and patent applications incorporated by reference herein. Representatives of metallotexaphyrin complexes included within the present invention are encompassed within the following structure I:

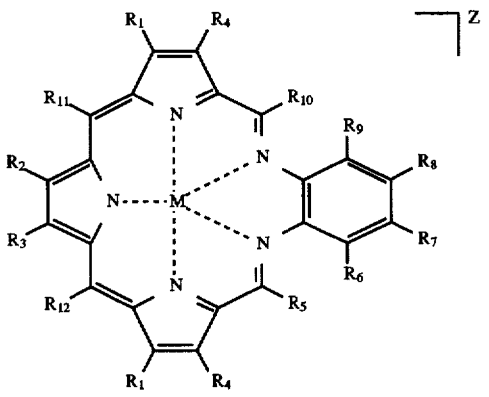

I

In this metallotexaphyrin complex, M is a divalent or a trivalent metal cation having catalytic activity for phosphate ester bond hydrolysis in aqueous solution.

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamide, carboxyamidealkyl, aminoalkyl, sulfonatoalkyl, amidealkyl, aryl, a site-directed molecule, a catalytic group, or a couple to a site-directed molecule or to a catalytic group.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple to a saccharide, to a site-directed molecule or to a catalytic group.

Z will typically be less than or equal to 5. In the context of the basic macrocycle with a divalent or trivalent metal cation, Z is 1 or 2; however, one skilled in the art in light of the present disclosure would realize that the complexes described in the present invention may have one or more additional ligands providing charge neutralization and/or coordinative saturation to the metal ion. Such ligands include chloride, nitrate, acetate, and hydroxide, among others. The value of Z would also be altered due to charges present on, for example, a covalently attached site-directed molecule, such as negative charges of the phosphate groups on an oligonucleotide.

In a preferred embodiment, at least one of $R_1$–$R_{12}$ is a site-directed molecule or is a couple to a site-directed molecule. For bulky R groups on the benzene ring portion of the molecule such as antibodies, peptides or oligonucleotides, one skilled in the art would realize that derivatization at one position on the benzene portion is more preferred.

"Alkyl" means alkyl groups, straight, branched or as cyclic isomers, with generally one to fifty, preferably one to thirty, more preferably one to ten, carbon atoms.

"Alkenyl" means alkenyl groups, straight, branched or as cyclic isomers, with generally two to fifty, preferably two to thirty, more preferably two to ten, carbon atoms, and with one to five or more double bonds, preferably one to five, more preferably one to three double bonds.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$alkyls being preferred, and diols of $C_{1-3}$alkyls being more preferred; and polyethylene glycol, polypropylene glycol and polybutylene glycol as well as polyalkylene glycols containing combinations of ethylene, propylene and butylene.

"Oxyalkyl" means alkyl groups as herein described with oxygen atoms, including ether or ester linkages. The number of repeating oxyalkyls within a substituent may be up to 200, preferably from 1 to 20, more preferably from 1 to 7, and most preferably is 2–3.

"Hydroxyalkoxy" means alkyl groups as described herein having ether or ester linkages, as well as hydroxyl groups, substituted hydroxyl groups, carboxyl groups, substituted carboxyl groups or the like.

"Carboxy" groups include carboxylic acids of the alkyls described herein as well as aryl carboxylic acids such as benzoic acid. "Carboxyalkyl" means alkyl groups having hydroxyl groups, carboxyl or amide substituted ethers, ester linkages, tertiary amide linkages removed from the ether or the like. Representative examples of "carboxyamides" include primary carboxyamides ($CONH_2$), and secondary (CONHR') and tertiary (CONR'R") carboxyamides where each of R' and R" is a functional group as described herein. "Carboxyamidealkyl" means alkyl groups with hydroxyl groups, secondary or tertiary amide linkages or the like.

Representatives of useful amines include a primary, secondary or tertiary amine of an alkyl as described hereinabove.

"Aryl" may be a phenyl group, unsubstituted or substituted with a nitro, carboxy, sulfonic acid, hydroxy, oxyalkyl, or halide.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides; as well as open chain forms of various sugars, and the like. Examples of amine-derivatized sugars are galactosamine, glucosamine, and sialic acid.

"Carboxyamidealkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether, or the like.

For the above-described texaphyrins, hydroxyalkoxy may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to ((2n+1)–2x). The hydroxyalkoxy or saccharide may be $C_nH_{((2n+1)-q)}O_yR^a{}_q$, $OC_nH_{((2n-1)-q)}O_yR^a{}_q$ or $(CH_2)_nCO_2R^a$ where n is a positive integer from 1 to 10, y is zero or a positive integer less than ((2n+1)–q), q is zero or a positive integer less than or equal to 2n+1, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to ((2m+1)–2w), and R is H, alkyl, hydroxyalkyl, or $C_mH_{((2m+1)-r)}O_zR^b{}_r$ where m is a positive integer from 1 to 10, z is zero or a positive integer less than ((2m+1)–r), r is zero or a positive integer less than or equal to 2m+1, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_n$ $CONHR^a$, $(CH_2)_nCON(R^a)_2$, or $O(CH_2)_nCON(R^a)_2$ where n is a positive integer from 1 to 10, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, $N(R)OCC_{(m-w)}H_{((2m+1)-2w)}O_wO_z$, or a site-directed molecule or catalytic group. In this case, m is a positive integer from 1 to 10, w is zero or a positive integer less than or equal to m, z is zero or a positive integer less than or equal to ((2m+1)−2w), and R is H, alkyl, hydroxyalkyl, or $C_mH_{((2m+1)-r)}O_zR^b{}_r$. In this case, m is a positive integer from 1 to 10, z is zero or a positive integer less than ((2m+1)−r), r is zero or a positive integer less than or equal to 2m+1, and $R^b$ is independently H, alkyl, hydroxyalkyl, or saccharide. In a preferred embodiment, $R^a$ is an oligonucleotide.

Carboxyalkyl may be alkyl having a carboxyl substituted ether, an amide substituted ether or a tertiary amide removed from an ether or $C_nH_{((2n+1)-q)}O_yR^c{}_q$ or $OC_nH_{((2n+1)-q)}O_yR^c{}_q$ where n is a positive integer from 1 to 10; y is zero or a positive integer less than ((2n+1)−q), q is zero or a positive integer less than or equal to 2n+1, and $R^c$ is $(CH_2)_nCO_2R^d$, $(CH_2)_nCONHR^d$, $(CH_2)_nCON(R^d)_2$ or a site-directed molecule or catalytic group. In this case, n is a positive integer from 1 to 10, $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to ((2m+1)−2w), and R is H, alkyl, hydroxyalkyl, or $C_mH_{((2m+1)-r)}O_zR^b{}_r$. In this case, m is a positive integer from 1 to 10, z is zero or a positive integer less than ((2m+1)−r), r is zero or a positive integer less than or equal to 2m+1, and $R^b$ is independently H, alkyl, hydroxyalkyl, or saccharide. In a preferred embodiment, $R^c$ is an oligonucleotide.

Hydrolytic cleavage of phosphate ester bonds, and particularly of RNA, by texaphyrin-metal complexes may be enhanced by additional catalytic groups appended to the texaphyrin-metal complex or to a texaphyrin complex-site directed molecule conjugate. The term "catalytic group" means a chemical functional group that assists catalysis by acting as a general acid, Brϕnsted acid, general base, Brϕnsted base, nucleophile, or any other means by which the activation barrier to reaction is lowered or the ground state energy of the substrate is increased. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, $(LysAla)_n$, $(LysLeuAla)_n$ where n is from 1–30 or preferably 1–10 or more preferably 2–7 and the like; derivatives thereof; and metallotexaphyrin complexes. The term "appended to the texaphyrin complex-site directed molecule conjugate" means that the catalytic groups are attached either directly to the metallotexaphyrin complex or to the texaphyrin complex via a linker or couple of variable length, or are attached to the site-directed molecule portion of a texaphyrin complex-conjugate either with or without a linker or couple of variable length.

Exemplary site-directed molecules useful herein include, but are not limited to, polydeoxyribonucleotides; oligodeoxyribonucleotides; polyribonucleotide analogs; oligoribonucleotide analogs; polyamides; molecules having affinity for a biological receptor, such as peptides, enzyme inhibitors, and proteins such as antibodies; steroids and steroid derivatives; hormones such as estradiol or histamine, and hormone mimics such as morphine; and further macrocycles such as sapphyrins and rubyrins.

The oligonucleotides may be derivatized at the bases, the sugars, the ends of the chains, or at the phosphate groups of the backbone to promote in vivo stability. Modifications of the phosphate groups are preferred in one embodiment since phosphate linkages are sensitive to nuclease activity. Presently preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy or propoxy. The alkenyl group is preferably allyl. The alkyl group is preferably a methyl group and the methyl group is attached to the 2' oxygen of the ribose. Other alkyl groups may be ethyl or propyl.

It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates and phosphoramidates and the like. Deoxyribonucleotides, deoxyribonucleotide analogs and ribonucleotide analogs are contemplated as site-directed molecules in the present invention.

The term "metallotexaphyrin-oligonucleotide conjugate" means that an oligonucleotide is attached to the texaphyrin in a 5' or a 3' linkage, or in both types of linkages to allow the texaphyrin to be an internal residue in the conjugate. It can also refer to a texaphyrin that is linked to an internal base of the oligonucleotide. The oligonucleotide or other site-directed molecule may be attached either directly to the texaphyrin or to the texaphyrin via a linker or a couple of variable length. During catalysis, for example, the texaphyrin portion of a texaphyrin-metal complex-oligonucleotide conjugate is placed in the vicinity of the substrate upon binding of the oligonucelotide to the targeted nucleic acid substrate.

A conjugate group having site specificity or catalytic activity may be covalently coupled to a texaphyrin directly on the macrocycle ring or through various couples. A couple may be described as a linker, i.e., the covalent product formed by reaction of a reactive group designed to attach covalently another molecule at a distance from the texaphyrin macrocycle. Exemplary linkers or couples are amides, amine, thiol, thioether, ether, or phosphate covalent bonds as described in the examples for attachment of oligonucleotides. In preferred embodiments, conjugates and appended groups are covalently bonded to the texaphyrin via a carbon-carbon, a carbon-nitrogen, a carbon-sulfur, or a carbon-oxygen bond, more preferred being a carbon-oxygen or a carbon-nitrogen bond.

In an embodiment of the present invention, M may be a divalent metal cation selected from the group consisting of $Ca^{+2}$, $Mn^{+2}$, $Co^{+2}$, $Ni^{+2}$, $Zn^{+2}$, $Cd^{+2}$, $Hg^{+2}$, $Fe^{+2}$, $Sm^{+2}$ and $UO_2{}^{+2}$ or a trivalent metal cation selected from the group consisting of $Mn^{+3}$, $Co^{+3}$, $Ni^{+3}$, $Fe^{+3}$, $Ho^{+3}$, $Ce^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^{+3}$, $Tm^{+3}$, $Yb^{+3}$, $Lu^{+3}$, $La^{+3}$, and $U^{+3}$. In particular, the metal may be La(III), Nd(III), Sm(III), Gd(III), Tm(III), or Lu(III), or preferably, Y(III), Tb(III), Eu(III) or Dy(III).

In presently preferred texaphyrins, $R_1$ is hydroxyalkyl and $R_2$, $R_3$ and $R_4$ are alkyl. Alternatively, $R_3$ may be a site-directed molecule or a couple to a site-directed molecule, preferably an oligonucleotide or a couple to an oligonucleotide. In a further presently preferred texaphyrin, $R_1$ is $CH_2CH_3$ or $(CH_2)_2CH_2OH$, $R_2$ and $R_3$ are $CH_2CH_3$, $R_4$ is $CH_3$, and $R_7$ and $R_8$ are $OCH_2CH_2CH_2OH$ or $R_7$ and $R_8$ are $O(CH_2CH_2O)_tCH_2CH_2OR'$ where t is 0–200, preferably 2–100, and R' is H or $CH_3$. Alternatively, $R_7$ is a site-directed molecule or a couple thereto, preferably an oligonucleotide or a couple thereto, more preferably $O(CH_2)_nCO$-oligonucleotide where n is 1–7 and preferably 1–3; and $R_8$ is H, $CH_3$ or $OCH_3$. In a further presently preferred embodiment, $R_1$ is $CH_2CH_3$ or $(CH_2)_2CH_2OH$, $R_2$ and $R_3$ are $CH_2CH_3$, $R_4$ is $CH_3$, $R_7$ is $O(CH_2CH_2O)_tCH_2CH_2OR'$ where t is 0–200, preferably 2–100, and R' is H or $CH_3$, and $R_8$ is a site-directed molecule or a couple thereto, preferably an oligonucleotide or a couple thereto, more preferably $O(CH_2)_nCO$-oligonucleotide where n is 1–7 and preferably 1–3.

In a further embodiment of the present invention, at least one of $R_1$–$R_{12}$ is a site-directed molecule or is a couple to a site-directed molecule. In a more preferred embodiment, the site-directed molecule is an oligonucleotide or is a couple to an oligonucleotide and most preferably, the oligonucleotide is a deoxyribonucleotide and the phosphate ester to be cleaved is RNA. The oligonucleotide has complementary binding affinity for the RNA in a region proximal to the phosphate ester bond being hydrolyzed. The oligonucleotide may have complementary binding affinity for viral RNA, in particular, retroviral RNA, or for bacterial ribosomal RNA, thereby cleaving the viral RNA or bacterial RNA and killing the organism. The oligonucleotide may have complementary binding affinity for mRNA, thereby cleaving the mRNA and modulating or interfering with the activity of the RNA such as, for example, the translation of mRNA into a protein. When the phosphate ester is RNA, the metal cation is preferably yttrium or a lanthanide metal cation, more preferably, Y(III), Tb(III), Eu(III) or Dy(III).

The oligonucleotide may be a deoxyribonucleotide and have complementary binding affinity for oncogenes. The site-directed molecule may have binding specificity for localization to a treatment site and the biological receptor may be localized to a treatment site.

Water-soluble texaphyrins are often preferred for the applications described herein, particularly when in vivo administration and treatment are contemplated. "Water-soluble" means soluble in aqueous fluids to about 1 mM or better. Such characteristics allow these texaphyrins to be useful in a biological environment. Improved water solubility can be achieved by, for example, substituents chosen from saccharides or hydroxylated substituents.

Although a survey of lanthanide (III) texaphyrin complexes indicates that all of the metal complexes examined are capable of hydrolytically cleaving RNA, complexes of terbium(III) and dysprosium(III) cleave RNA faster than other lanthanides of those tested thus far. Additionally, while it is believed that complexes of lanthanoid metals will also cleave RNA hydrolytically, it has been found that yttrium (III) complexes perform very well.

While all of the above-described texaphyrins are presently preferred compounds, the invention is not limited thereto and any metallotexaphyrin complex having catalytic activity for phosphate ester hydrolysis may be useful in the practice of the invention.

An individual skilled in the art of organic synthesis in light of the present disclosure is able to prepare a large variety of texaphyrins and metallotexaphyrin complexes, which are expected to hydrolytically cleave phosphate esters, an important biological species.

Texaphyrin compounds and methods for making are described in U.S. Pat. Nos. 4,935,498, 5,162,509, 5,252,720, 5,272,142 and 5,256,399, each of which is incorporated by reference herein.

Generally, the introduction of hydroxy substituents on the B (benzene ring) portion of the texaphyrin molecule is accomplished by their attachment to phenylenediamine in the 4 and 5 positions of the phenyl subunit of the molecule or they may be added in a synthetic step following the condensation step that forms the macrocycle metal complex as described in the above-named patents. The introduction of hydroxy substituents on the T (tripyrrole or tripyrrane) portion of the molecule is accomplished by appropriate functionalization of the alkyl substituents in the 3 and/or 4 positions of the pyrrole rings at a synthetic step prior to condensation with the substituted phenylenediamine. Standard deprotection methodology such as ester hydrolysis may be used to unmask free hydroxyl substituents. Alternatively, they may be prepared as the result of ester reduction. These derivatives exhibit significant solubility in aqueous media, up to 1 mM or better, yet they retain affinity for lipid-rich regions which allows them to be useful in biological environments.

One skilled in the art of organic synthesis in light of the present disclosure and the disclosures in the patents, applications and publications incorporated by reference herein could extend and refine the basic synthetic chemistry to produce texaphyrins having various substituents. For example, a doubly carboxylated texaphyrin in which the carboxyl groups are linked to the texaphyrin core via aryl ethers or functionalized alkyl substituents could be converted to various esterified products wherein the ester linkages serve to append further hydroxyl-containing substituents. Polyhydroxylated texaphyrin derivatives may be synthesized via the use of secondary amide linkages. Saccharide moieties may be appended via amide bonds. Polyhydroxylated texaphyrin derivatives containing branched polyhydroxyl (polyol) subunits may be appended to the texaphyrin core via aryl ethers or ester linkages.

Treatment of carboxylated texaphyrins with thionyl chloride or p-nitrophenol acetate would generate activated acyl species suitable for attachment to monoclonal antibodies or other biomolecules of interest. Standard in situ coupling methods (e.g., 1,1'-carbonyldiimidazole) could be used to effect the conjugation.

The selectivity of the texaphyrins may be enhanced by covalently linking oligonucleotides onto the periphery of the macrocycle. Amides, ethers and thioethers are representative of linkages which may be used for this purpose. Oligonucleotides functionalized with amines at the 5'-end, the 3'-end, or internally at sugar or base residues may be modified post-synthetically with an activated carboxylic ester derivative of the texaphyrin complex. Alternatively, oligonucleotide analogs containing one or more thiophosphate or thiol groups may be selectively alkylated at the sulfur atom(s) with an alkyl halide derivative of the texaphyrin complex. The resultant oligonucleotide-complex conjugates may be designed so as to provide optimal catalytic interaction between a target nucleic acid and the bound texaphyrin. The oligonucleotide may be large enough to bind probably at least about 9–12 nucleotides of complementary nucleic acid. Specific methods for preparing texaphyrin-oligonucleotide conjugates are disclosed in WO 94/29316, incorporated herein by reference.

The use of metallotexaphyrin complexes to hydrolyze phosphate esters, such as RNA, in vivo as a treatment procedure relies on the effective localization of the complex to the site of desired cleavage. A site of desired cleavage may be a position novel to undesired organisms in terms of health care. A site of desired cleavage may be an RNA encoding a product deleterious to the host or may be a normal RNA that is deleterious in some way. Treating native RNA with the metallotexaphyrin complexes in a site-specific manner results in the metallotexaphyrin complex binding to a complementary RNA sequence via an appended oligonucleotide. The metallotexaphyrin complex then cleaves the RNA proximal to this specific site.

Texaphyrin metal complex-oligonucleotide conjugates (metallotexaphyrin-oligonucleotide conjugates) may be developed into antisense reagents useful in the present invention. This antisense strategy provides a clear and rational method for new drug design because there is one requirement, namely that the antisense probe hybridize to its target molecule. The hybridization requirement is very well understood via complementary Watson-Crick or Hoogsteen base pairing. Unlike the present methods in the art which require screening of thousands of compounds and X-ray crystal structure analysis, the information needed for antisense technology is the sequence of the target. Treating native RNA with a metallotexaphyrin-oligonucleotide conjugate results in the conjugate binding to a complementary RNA sequence via the appended oligonucleotide. The metallotexaphyrin complex then hydrolyzes the RNA proximal to this specific binding site. The metallotexaphyrin complex enhances the therapeutic activity of the antisense oligonucleotide, not only by facilitating cellular uptake of the oligonucleotide but also by hydrolyzing the target RNA within the cell independent of RNase H. Additionally, attachment to the texaphyrin complex causes the oligonucleotide antisense agent to take on some of the pharmacodynamic and biodistribution properties of the texaphyrin such as selective localization in tumors.

The metallotexaphyrin-oligonucleotide ribozyme analog approach to antisense therapy can be applied to virtually any oligonucleotide backbone and may overcome many of the known limitations of antisense-based therapies. By increasing oligonucleotide uptake in cells and enhancing the activity of the oligonucleotide, metallotexaphyrins should allow for the development of more efficacious antisense therapeutic products. The ribozyme analog sequence need only be of sufficient length to specifically recognize its RNA target, typically 12–15 residues. This is much shorter than actual ribozymes, which are considerably longer in order to contain the structural features necessary for catalytic activity. By selecting appropriate oligonucleotide backbones that recognize specific RNA sequences, the metallotexaphyrin ribozyme analog approach may be used in therapeutic approaches to cancer, viral diseases such as HIV and hepatitis, and other disorders such as autoimmune diseases and restenosis. Other applications of this technology include in vitro site-specific RNA cleavage for use in diagnostics or as reagents, such as custom-made restriction enzyme analogs.

The texaphyrin complex-oligonucleotide conjugates may be useful for inhibiting the expression of a gene in an animal or in a particular tissue of an animal. They are also useful in a method for targeted intracellular RNA hydrolysis, and especially intracellular messenger RNA hydrolysis.

The present method of hydrolysis would have immediate applications for anti-viral and anti-bacterial therapy as well as for cancers (an oligonucleotide complementary to an oncogene, for example) and inflammatory responses that are caused by the overexpression of certain proteins.

Exemplary texaphyrins useful in the present invention are listed in Tables A–C, see below.

TABLE A

Representative Substituents for Texaphyrin Macrocycles A1–A50 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2CH_3$ | $CH_2CH_3$ | $CH_3$ | H | COOH |
| A2 | " | " | " | " | " | COOH |
| A3 | " | " | " | " | " | $CONHCH—(CH_2OH)_2$ |
| A4 | " | " | " | " | " | " |
| A5 | " | " | " | " | " | H |
| A6 | " | " | " | " | " | $OCH_3$ |
| A7 | " | " | " | " | " | " |
| A8 | " | " | " | " | " | " |
| A9 | " | " | " | " | " | " |
| A10 | " | " | " | " | " | " |
| A11 | " | " | " | " | " | " |
| A12 | " | " | " | " | " | " |
| A13 | " | " | " | " | " | $CH_3$ |
| A14 | " | " | " | " | " | " |
| A15 | " | " | " | " | " | " |
| A16 | " | " | " | " | " | " |
| A17 | " | " | " | " | $CH_3$ | H |
| A18 | " | " | " | " | " | " |
| A19 | " | " | " | " | " | " |
| A20 | $CH_2(CH_2)_2OH$ | $CH_2CH_3$ | $CH_2CH_3$ | $CH_3$ | $CH_3$ | H |
| A21 | " | " | " | " | " | " |
| A22 | " | " | " | " | " | " |
| A23 | " | " | " | " | " | " |
| A24 | " | " | " | " | " | " |
| A25 | " | " | " | " | " | " |
| A26 | " | " | " | " | " | OH |
| A27 | " | " | " | " | " | F |
| A28 | " | " | " | " | $CH_2(CH_2)_6OH$ | H |
| A29 | " | " | " | " | H | Br |
| A30 | " | " | " | " | " | $NO_2$ |
| A31 | " | " | " | " | " | COOH |
| A32 | " | " | " | " | " | $CH_3$ |
| A33 | " | " | " | " | $C_6H_5$ | H |
| A34 | " | COOH | COOH | " | $CH_2CH_3$ | " |
| A35 | " | $COOCH_2CH_3$ | $COOCH_2CH_3$ | " | $CH_3$ | " |
| A36 | $CH_2CH_2CON(CH_2CH_2OH)_2$ | $CH_2CH_3$ | $CH_2CH_3$ | " | " | " |
| A37 | $CH_2CH_2ON(CH_3)CH_2—(CHOH)_4CH_2OH$ | " | " | " | " | " |

TABLE A-continued

Representative Substituents for Texaphyrin Macrocycles A1–A50 of the Present Invention. Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A38 | $CH_2CH_3$ | " | " | " | $CH_2(CH_2)_6OH$ | " |
| A39 | $CH_2(CH_2)_2OH$ | $CH_2CH_3$ | $CH_2CH_3$ | $CH_3$ | $CH_3$ or $CH_2CH_3$ | H |
| A40 | " | " | " | " | " | " |
| A41 | " | " | " | " | " | " |
| A42 | " | " | " | " | " | " |
| A43 | " | " | " | " | " | " |
| A44 | " | " | " | " | " | " |
| A45 | " | " | " | " | " | " |
| A46 | " | " | " | " | " | " |
| A47 | " | " | " | " | " | " |
| A50 | " | " | " | " | " | " |
| A51 | " | " | " | " | H | " |
| A52 | " | " | " | " | " | " |
| A53 | " | " | " | " | " | " |
| A54 | " | " | " | " | " | " |
| A55 | " | " | " | " | $CH_3$ or $CH_2CH_3$ | " |
| A56 | " | " | " | " | " | " |

TABLE B

Representative Substituents for Texaphyrin Macrocycles A1–A50 of the Present Invention. Substituents for $R_1$–$R_6$ Are Provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A1 | $O(CH_2)_3OH$ | $O(CH_2)_3OH$ | $O(CH_2)_3OH$ | H | H | H |
| A2 | $O(CH_2CH_2O)_3CH_3$ | $O(CH_2CH_2O)_3CH_3$ | COOH | " | " | " |
| A3 | $O(CH_2CH_2O)_3CH_3$ | $O(CH_2CH_2O)_3CH_3$ | O-saccharide | " | " | " |
| A4 | " | " | $O(CH_2CH_2O)_3CH_3$ | " | " | " |
| A5 | " | $O(CH_2)_3$CON-linker-oligo | " | " | " | " |
| A6 | H | $OCH_2$CON-linker-oligo | $OCH_3$ | " | " | " |
| A7 | " | $OCH_2$CO-poly-L-lysine | " | " | " | " |
| A8 | " | $OCH_2$CO-estradiol | " | " | " | " |
| A9 | " | $O(CH_2CH_2O)_3CH_3$ | " | " | " | " |
| A10 | $O(CH_2CH_2O)_3CH_3$ | " | " | " | " | " |
| A11 | " | $OCH_2$CON-linker-oligo | " | " | " | " |
| A12 | " | $OCH_2$CO-estradiol | " | " | " | " |
| A13 | " | $O(CH_2CH_2O)_3CH_3$ | $O(CH_2CH_2O)_3CH_3$ | " | " | " |
| A14 | " | $OCH_2$CO-estradiol | " | " | " | " |
| A15 | $O(CH_2CH_2O)_3CH_3$ | $O(CH_2CH_2O)_{120}CH_3$ | $OCH_3$ | " | " | " |
| A16 | H | saccharide | " | " | " | " |
| A17 | $O(CH_2)_3OH$ | $O(CH_2)_3OH$ | H | $CH_3$ | " | " |
| A18 | H | $O(CH_2CH_2O)_3CH_3$ | " | " | " | " |
| A19 | $O(CH_2CH_2O)_3CH_3$ | " | " | " | " | " |
| A20 | H | $OCH_2$CON-linker-oligo | H | $CH_3$ | " | " |
| A21 | " | $OCH_2$CO-estradiol | " | " | " | " |
| A22 | " | $OCH_2CON(CH_2CH_2OH)_2$ | " | " | " | " |
| A23 | $O(CH_2CH_2O)_3CH_3$ | $O(CH_2CH_2O)_{120}CH_3$ | " | " | " | " |
| A24 | " | $OCH_2$CON-linker-oligo | " | " | " | " |
| A25 | H | $CH_2CON(CH_3)CH_2$—<br>$(CHOH)_4CH_2OH$ | " | " | " | " |
| A26 | $O(CH_2CH_2O)_3CH_3$ | $O(CH_2CH_2O)_3CH_3$ | OH | " | " | " |
| A27 | " | " | F | " | " | " |
| A28 | " | " | H | $CH_2(CH_2)_6OH$ | " | " |
| A29 | " | " | Br | H | " | " |
| A30 | " | " | $NO_2$ | " | " | " |
| A31 | " | " | COOH | " | " | " |
| A32 | " | " | $CH_3$ | " | " | " |
| A33 | " | " | H | $C_6H_5$ | " | " |
| A34 | " | " | " | $CH_2CH_3$ | " | " |
| A35 | " | " | " | " | " | |
| A36 | " | " | " | " | " | " |
| A37 | $OCH_3$ | $OCH_3$ | " | " | " | " |
| A38 | H | $OCH_2CO_2$-glucosamine | " | $CH_2(CH_2)_6OH$ | " | " |
| A39 | $O(CH_2)_3OH$ | $O(CH_2)_3OH$ | H | $CH_3$ or $CH_2CH_3$ | $CH_3$ or $CH_2CH_3$ | $CH_3$ or $CH_2CH_3$ |
| A40 | $O(CH_2CH_2O)_3CH_3$ | $O(CH_2CH_2O)3CH_3$ | " | " | " | " |
| A41 | $O(CH_2)_3OH$ | $O(CH_2CH_2O)_3CH_3$ | " | " | " | " |
| A42 | H | $O(CH_2)_n$CON-linker-oligo,<br>n = 1,2,3 | " | " | " | " |
| A43 | H | $O(CH_2)_n$CO-estradiol,<br>n = 1,2,3 | " | " | " | " |

TABLE B-continued

Representative Substituents for Texaphyrin Macrocycles A1–A50 of the Present Invention.
Substituents for $R_1$–$R_6$ Are Provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A44 | H | saccharide | " | " | " | " |
| A45 | $O(CH_2)_3OH$ | $O(CH_2)_nCON$-linker-oligo, n = 1,2,3 | " | " | " | " |
| A46 | " | $O(CH_2)_nCO$—estradiol, n = 1,2,3 | " | " | " | " |
| A47 | " | saccharide | " | " | " | " |
| A48 | $O(CH_2CH_2O)_3CH_3$ | $O(CH_2)_nCON$-linker-oligo, n = 1,2,3 | " | " | " | " |
| A49 | " | $O(CH_2)_nCO$-estradiol, n = 1,2,3 | " | " | " | " |
| A50 | " | saccharide | " | " | " | " |
| A51 | " | $O(CH_2)_nCON$-linker-oligo n = 1,2,3 | " | H | " | " |
| A52 | " | $O(CH_2CH_2O)_3CH_3$ | " | " | " | " |
| A53 | " | " | " | " | $CH_2(CH_2)_2OH$ | $CH_2(CH_2)_2OH$ |
| A54 | " | $O(CH_2)_nCON$-linker-oligo n = 1,2,3 | " | " | " | " |
| A55 | " | $O(CH_2)_n$-linker-oligo n = 1,2,3 | " | $CH_3$ or $CH_2CH_3$ | " | " |
| A56 | " | $O(CH_2CH_2O)_3CH_3$ | " | " | " | " |

TABLE C

Representative Substituents for
Texaphyrin Macrocycles of the Present Invention
($R_5$, $R_6$, and $R_9$–$R_{12}$ are H)

| TXP | $R_1$ | $R_2$ | $R_3$ | $R_4$ | $R_7$ | $R_8$ |
|---|---|---|---|---|---|---|
| B1 | $CH_2(CH_2)_2OH$ | $CH_2CH_3$ | $CH_2CH_3$ | $CH_3$ | $O(CH_2)_3OH$ | $O(CH_2)_3OH$ |
| B2 | " | " | " | " | $O(CH_2CH_2O)_3CH_3$ | $O(CH_2CH_2O)_3CH_3$ |
| B3 | " | " | " | " | $O(CH_2)_nCON$-linker-site-directed molecule, n = 1–7 | " |
| B4 | " | " | " | " | $O(CH_2)_nCON$-linker-site-directed molecule | H |
| B5 | " | " | " | " | $OCH_2CO$-poly-L-lysine | " |
| B6 | " | " | " | " | $OCH_2CO$-hormone | " |
| B7 | " | " | " | " | $O(CH_2CH_2O)_3CH_3$ | " |
| B8 | " | " | " | " | $OCH_2CON$-linker-site-directed molecule | $O(CH_2CH_2O)_3CH_3$ |
| B9 | " | " | " | " | $OCH_2CO$-hormone | " |
| B10 | " | " | " | " | $OCH_2CON$-oligo | $O(CH_2CH_2O)_3CH_2$—$CH_2$—N-imidazole |
| B11 | " | " | " | " | $O(CH_2CH_2O)_{120}CH_3$ | $O(CH_2CH_2O)_3CH_2$—$CH_2$—N-imidazole |
| B12 | " | " | " | " | saccharide | H |
| B13 | " | " | " | " | $OCH_2CON(CH_2CH_2OH)_2$ | " |
| B14 | " | " | " | " | $CH_2CON(CH_3)CH_2$—$(CHOH)_4CH_2OH$ | " |
| B15 | " | COOH | COOH | " | $CH_2CON(CH_3)CH_2$—$(CHOH)_4CVH_2OH$ | " |
| B16 | " | $COOCH_2$—$CH_3$ | $COOCH_2$—$CH_3$ | " | $CH_2CON(CH_3)CH_2$—$(CHOH)_4CH_2OH$ | " |
| B17 | $CH_2CH_2CON$ $(CH_2$ $CH_2OH)2$ | $CH_2CH_3$ | $CH_2CH_3$ | " | $CH_2CON(CH_3)CH_2$—$(CHOH)_4CH_2OH$ | " |
| B18 | $CH_2CH_2ON(CH_3)$ $CH_2$—$(CHOH)$ $_4CH_2OH$ | " | " | " | $OCH_3$ | $OCH_3$ |
| B19 | $CH_2CH_3$ | " | " | " | $OCH_2CO_2$-glucosamine | H |
| B20 | $CH_2(CH_2)_2OH$ | " | " | " | $O(CH_2)_nCOOH$, n = 1–7 | " |
| B21 | " | " | " | " | $(CH_2)_n$—CON-linker-site-directed molecule, n = 1–7 | " |
| B22 | " | " | " | " | $YCOCH_2$-linker-site-directed molecule Y=NH,O | " |
| B23 | $CH_2CH_3$ | $CH_3$ | $CH_2CH_2$— | " | $O(CH_2)_2CH_2OH$ | $O(CH_2)_2CH_2OH$ |

TABLE C-continued

Representative Substituents for Texaphyrin Macrocycles of the Present Invention ($R_5$, $R_6$, and $R_9$-$R_{12}$ are H)

| TXP | $R_1$ | $R_2$ | $R_3$ | $R_4$ | $R_7$ | $R_8$ |
|---|---|---|---|---|---|---|
| | | | COOH | | | |
| B24 | " | " | $CH_2CH_2$—CON-oligo | " | " | " |
| B25 | $CH_2(CH_2)_2OH$ | $CH_2CH_3$ | $CH_2CH_3$ | " | $OCH_2COOH$ | $O(CH_2CH_2O)_3CH_2$—$CH_2$—N-imidazole |
| B26 | " | " | " | " | $O(CH_2)_3CO$-histamine | H |
| B27 | " | " | " | " | $O(CH_2)_3CO$-arginine methyl ester | " |
| B28 | " | " | " | " | $O(CH_2)_nCO$-amino acid, n = 1–7 | " |
| B29 | " | " | " | " | $O(CH_2)_nCON$-catalytic group, n = 1–7 | " |

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE 1

Hydrolysis of Monoesters by Lanthanide(III) T2B2 Texaphyrin

The present example provides the utility of the present invention in the use of metallotexaphyrin complexes for the hydrolysis of monoesters, in particular, the hydrolysis of UpU, cUMP, 3'-UMP and 2'-UMP.

Cytosine, uridine, uridine-2'- and -3'-monophosphate disodium salt (2'-UMP and 3'-UMP), uridine-2',3'-cyclicmonophosphate sodium salt (cUMP), and uridylyl (3'→5') uridine ammonium salt (UpU) were purchased from Sigma (St. Louis, Mo.) and used without further purification. The lanthanide texaphyrins were prepared as described in detail in WO 94/29316, the entire disclosure of which is incorporated herein by reference. All solutions, unless otherwise stated, were prepared from a stock solution of 5.0 mM N-(2-hydroxyethyl)piperazine-N'-ethanesulfonic acid (HEPES), in Milli-Q purified water, adjusted to pH 7.0. Solutions were stored and reactions conducted in RNAse-free plastic vials further sterilized by heating at 120° C. for 20 minutes in an autoclave. Gloves were worn at all times during solution preparation and reaction sampling. All kinetic runs were thermostatted at 37° C. in a water bath.

High-performance liquid chromatography (HPLC) was performed on a Waters 501 equipped with a Waters model 440 absorbance detector, monitoring at 254 nm. A YMC, Inc., USA ODS-AQ column (150 mm×4.6 mm I.D.) was used. Satisfactory separation was achieved with an isocratic gradient (10 mM $NaH_2PO_4$ adjusted to pH 5.6 with 1% methanol) with a flow rate of 1.0 ml/min. A Beckman DU-7 spectrometer was used to confirm the concentrations of EuB2T2 txp.

Eu $(NO_3)_3$. In the control experiment, the reaction solutions were prepared by diluting 100 μL of UpU (2.94 mM), 25 μL of $Eu(NO_3)_3$ (3.5 μm), and 100 μL of cytosine (0.423 mM), as internal standard, in 375 μL of 5.0 mM HEPES solution. The reactions were carried out as for EuB2T2 txp. The pseudo-zero order rate constant for the control reaction was determined to be $k=(2.2\pm0.8)\times10^{-4}$ mM/hr.

EuB2T2 txp. Europium(III) B2T2 texaphyrin ("EuB2T2 txp", cpd. $8_A$) was prepared and described in WO 94/29316.

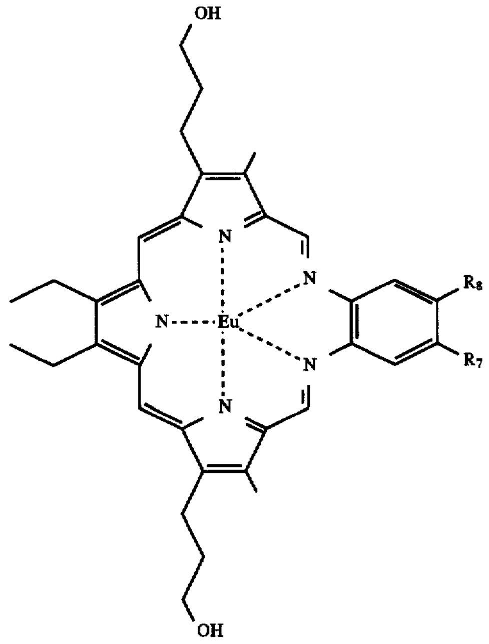

$8_A$ $R_7 = R_8 = OCH_2CH_2CH_2OH$ ("EuB2T2 txp")
$8_B$ $R_7 = H, R_8 = OCH_2CO_2H$
$8_C$ $R_7 = H, R_8 = OCH_2CO$-DNA In a typical kinetics experiment, the reaction solutions were prepared by diluting 100 μL of UpU (2.94 mM), 50 μL of EuB2T2 txp (7.8 mM), and 100 μL of cytosine (0.423 mM), as internal standard, in 350 μL of 5.0 mM HEPES solution. The rate of UpU hydrolysis was monitored by removing 15 μL aliquots which were frozen until HPLC analysis was possible. All samples were microfiltered (0.2 μm) prior to injection on the HPLC. All runs were performed in triplicate. The background as determined from the simultaneous control containing no metal complex was negligible. The pseudo-zero order rate constant for the reaction was determined to be k=(9.1±1.6)×$10^{-4}$ mM/hr at 37° C., pH 7.0.

The pseudo-zero order rate constant for the hydrolytic cleavage of a ribodinucleotide by the nitrate salt of the water-soluble EuB2T2 texaphyrin was examined. Investigations indicated that a 0.15 mM aqueous solution of Eu(B2T2 $txp)^{2+}$ hydrolytically cleaved uridylyl (3'→45') uridine, UpU, (0.49 mM) with a pseudo-zero zero order rate of (9.1±1.6)×$10^{-4}$ mM/hr at 37° C., pH 7.0. In the absence of the metal complex no evidence of RNA cleavage was observed by HPLC. The reaction was followed by HPLC, monitoring the formation of uridine. Uridine-2'-monophosphate, uridine-3'-monophosphate, and uridine-2',3'-cyclicmonophosphate (cUMP) were also observed by HPLC; this indicates a hydrolytic rather than an oxidative mechanism for the cleavage reaction. Uridine-2',3'-cyclicmonophosphate reached a steady state concentration, implying that the texaphyrin complex hydrolyzed cUMP as well. Under identical conditions, a 0.15 mM aqueous solution of $Eu(NO_3)_3$ has a pseudo-zero order rate constant of (2.2±0.35)×$10^{-4}$ mM/hr. Therefore, small traces of free metal ions cannot account for the hydrolysis observed in the presence of the metallotexaphyrin complex. Under these conditions, the Eu(III) complex of HAM displayed a pseudo-zero order rate constant of 4.1×$10^{-4}$ mM/hr. Thus, the texaphyrin complex is found to be more effective than the HAM system.

A survey of other lanthanide (III) complexes of B2T2 texaphyrin indicated that these complexes are also capable of RNA hydrolysis. Results are summarized in Table 2.

TABLE 2

Rate Constants (Pseudo-Zero Order) for the Hydrolysis of UPU by Lanthanide(III) B2T2 Texaphyrin Complexes[a]

| LANTHANIDE CATION | k mM/h |
|---|---|
| La(III) | 1.16 × $10^{-4}$ |
| Nd(III) | 4.69 × $10^{-4}$ |
| Sm(III) | 6.3 × $10^{-4}$ |
| Eu(III) | 4.99 × $10^{-3}$ |
| Gd(III) | 1.44 × $10^{-4}$ |
| Dy(III) | 6.0 × $10^{-3}$ |
| Tm(III) | 4.16 × $10^{-4}$ |
| Lu(III) | 1.91 × $10^{-4}$ |

[a]The concentrations of the Lanthanide(III)B2T2 $txp(NO_3)_2$ were all approximately 0.25 mM.

Further evidence supporting the catalytic effect of the metallotexaphyrin complex was obtained by monitoring the formation of uridine produced from the $Eu(T2B2Txp)^{+2}$ catalyzed decomposition of uridine-2',3'-cyclicmonophosphate (cUMP). The decomposition of cUMP (0.10 mM) catalyzed by $Eu(T2B2Txp)^{+2}$ (0.15 mM), when incubated at 37° C. and pH=7.0 (5 mM HEPES buffer), had a pseudo-zero order rate of 6.94×$10^{-5}$ $mMh^{-1}$ for the production of uridine. Examination of the reaction products by HPLC indicated that initially cUMP is isomerized to uridine-3'-monophosphate (3-UMP) and uridine-2'-monophosphate (2'-UMP), which are subsequently hydrolytically cleaved to produce uridine, as illustrated below.

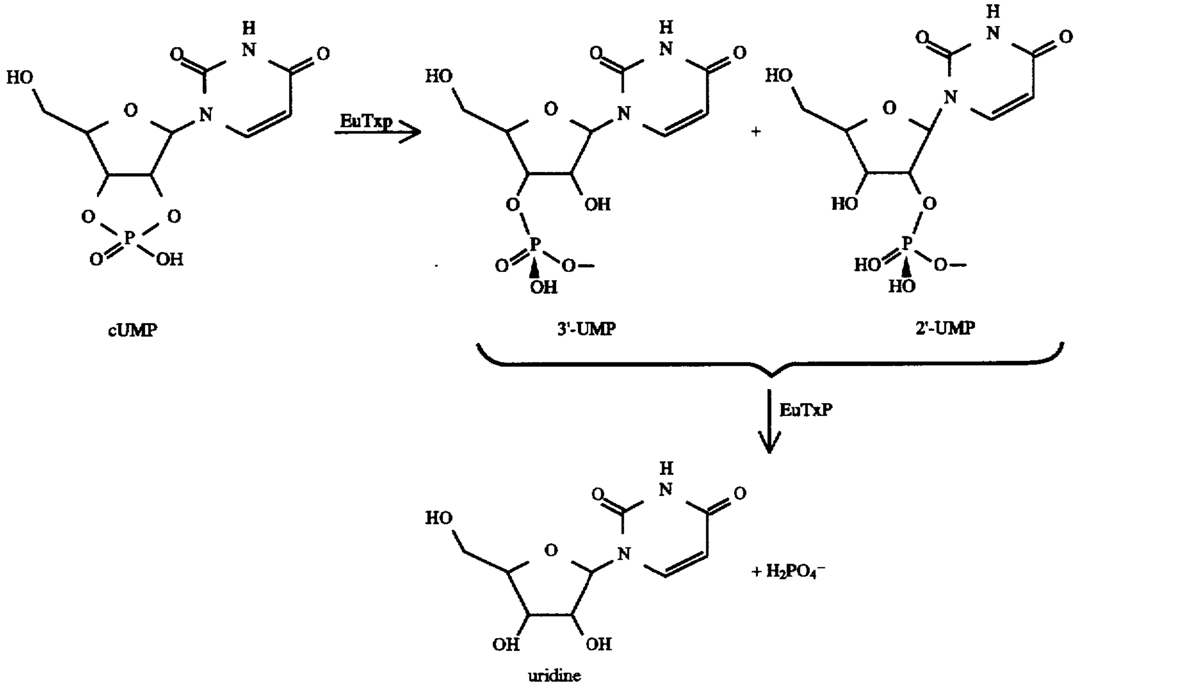

cUMP 3'-UMP 2'-UMP uridine

EXAMPLE 2

Generalized Hydrolysis of RNA Using a Metallotexaphyrin Complex

This example describes the degradation of a homogenous population of RNA molecules with EuB2T2 texaphyrin. $P^{32}$-labelled RNA transcripts from an isolated clone was the homogenous RNA substrate. The transcripts and their degradation products were visualized by polyacrylamide gel electrophoresis and autoradiography.

pGEM®-3Z vector and Riboprobe® RNA transcript systems were obtained from Promega Corporation, Madison, Wis. A 4.3 kb fragment of the mouse 1b Multi Drug Resistant gene (MDR) was cloned into the EcoRI site of the pGEM 3Z vector and its orientation determined (see FIG. 1). The plasmid was used in transcription reactions and, when digested with BamHI, T7 RNA polymerase makes a transcript from this template that is approximately 2000 bases long. The transcription reaction consisted of 100 ng of BamHI digested pGEM 3Z/4.3 MDR#3, 20 µL of 5× transcription buffer, triphosphate nucleotides (A,C,G) at 500 µM, UTP at 100 µM, 50 µC of $^{32}$-P α-UTP (3000 Ci/mmol), 10 mmol DTT, 120 units of RNasin and 70–100 units T7 RNA polymerase. This reaction was brought up to a total volume of 100 µL with DEPC treated double distilled water. The reaction was allowed to incubate at 37° C. for 1.5 hours. The entire reaction volume was then run over a G-50 Sephadex column (Nick column, Pharmacia) pre-equilibrated with 20 mM Tris pH 7.0, 2 mM EDTA, 0.1% SDS. The transcript was eluted from the column in the second 400 µL volume applied to the column. Any unincorporated nucleotide was left on the column.

Ten-µL aliquots of the transcript were put into separate tubes, and stock solutions of EuB2T2txp, EDTA or Eu(III) acetate (EuOAc) were added so that the final volume was 20 µL. The tubes were allowed to incubate for 2 hr at 37° C. Thirty µL of dye mix (formamide, 0.2% bromphenol blue) was added to each tube. The tubes were mixed and heated at 60° C., 5 min, then the entire content of the reaction was loaded onto a 5% 8M urea polyacrylamide gel and electrophoresis was performed. The gel was set up as follows: Lane 1, control, no EuB2T2 txp; lane 2, control with EDTA; lanes 3–7, EuB2T2 txp, 100 µM, 50 µM, 25 µM, 10 µM and 5 µM; lanes 8–10, EuB2T2 txp, 100 µM and EDTA at 500 µM, 300 µM and 100 µM; lane 11, M.W. std; lane 12, control, no EuB2T2 txp; lane 13, EuB2T.2 txp, 100 µM and EDTA, 10 µM.

The results of the digests of the 2000 base long transcripts with EuB2T2 txp were as follows: There was one band in the control and control with EDTA lanes 1, 2 and 12. This band was absent in the lane with 100 µM EuB2T2 txp, lane 3. An increase in lower molecular weight material, i.e. degradation products, was seen as smearing throughout lane 3. The transcript remained intact at the lower EuB2T2 txp concentrations, lanes 4–7. The transcript was degraded with 100 µM EuB2T2 txp in the presence of 500, 300, 100 and 10 µM amounts of EDTA, lanes 8–10 and 13. This experiment eliminates the possibility that free metal in the EuB2T2 txp solution was causing the degradation. Lane 11 contained molecular weight standards of 1418 and 679 bases. The 100, 50, 25, 10 and 5 µM concentrations of free europium metal salt (EuOAc) did not digest the transcript, lanes 3–7. These results were not affected by the presence of EDTA.

A digestion of total RNA (primarily 28s and 18s ribosomal RNA from K562 cells) with EuOAc, EuT2B2 txp and GdT2B2 txp indicated that all are able to hydrolyze total RNA. The digestions were performed in 50% DMSO and $H_2O$, and the gel was electrophoresed using a 10 µM phosphate buffer, pH 6.8. It is likely that EuOAc digests the homogeneous transcript also but at higher EuOAc concentrations than those used in the present example.

Clearly, EuB2T2 txp is able to hydrolyze RNA substrates. Since the texaphyrins have such versatility for functionalization, this result has significant implications for the construction of site-specific cleaving reagents for nucleic acids and other molecules as discussed further in the following examples.

EXAMPLE 3

Site-Specific Hydrolysis of RNA by Europium(III)-Texaphyrin Conjugated to a Synthetic Oligodeoxyribonucleotide The present example provides antisense agents using a metallotexaphyrin complex-oligonucleotide conjugate that effects the hydrolysis of its RNA complement. Such antisense agents should therefore be able to act in vivo without the participation of endogenous nucleases. A EuTx-DNA oligonucleotide conjugate was synthesized based on the functionalized texaphyrin $8_B$. This "ribozyme analogue" (cf., $8_C$) provides an example of oligodeoxynucleotide-directed, metal-catalyzed hydrolysis of a complementary RNA oligomer.

Two 20-mer oligonucleotides were machine-synthesized to contain alkylamine groups at either the 5-position of an internal thymine residue or the 5'-end terminal phosphate. Oligodeoxynucleotide-amines modified on the 5-position of thymine were purchased from Oligo's Etc. (Wilsonville, Oreg.); oligodeoxynucleotide-amines modified on the 5' end were purchased from Keystone Laboratories, Inc. (Menlo Park, Calif.). Oligonucleotides were HPLC purified and precipitated using LiCl prior to use. Reaction of the carboxylic acid functionalized europium(III) texaphyrin complex $8_B$ with carbodiimide and N-hydroxysuccinimide produced the corresponding activated ester, which was added directly to a solution of the chosen oligodeoxynucleotide amine. The resulting DNA-EuTx conjugates (FIG. 2, $9_{A-D}$) were purified by electrophoresis.

A synthetic RNA 30-mer ($10_B$, FIG. 3) was obtained as substrate (Keystone Labs, Inc., Menlo Park, Calif.), with a sequence selected from a unique site within the gene transcript for multiple drug resistance. The sequence is complementary at 1562 bases post-transcriptional start site in mouse multidrug resistance protein mRNA. The 3'-$^{32}$P-labelled substrate was incubated with an excess of oligodeoxynucleotide conjugate at 37° C. for 18–24 hr in a buffered salt solution, precipitated with ethanol, and assayed on a 20% denaturing polyacrylamide gel. Ca. $1.5\times10^5$ cpm of substrate was incubated in a total volume of 20 µL of buffer containing 50 mM HEPES, pH 7.5, 100 mM NaCl, 25 µM EDTA and 5 µg/mL calf thymus DNA. Lane 1, no DNA, control; lane 2, control with unmodified oligodeoxynucleotide $9_E$; lane 3, 2.5 µM $8_B$; lane 4, 25 µM $8_B$; lanes 5–7, $9_E$ and, respectively, 250 nM, 2.5 µM, and 25 µM of $8_B$; lane 8, $9_A$; lane 9, $9_C$; lane 10, $9_B$; lanes 11–14, $9_D$ at 2.5 nM, 25 nM, 250 nM, and 2.5 µM, respectively. All other oligonucleotides were at 2.5 µM final concentration. Nucleotide sequence analysis was determined by partial digestion with base-specific ribonucleases: T1(G); U2 (A>G); Phy M (U+A); B. cereus (U+C); $HCO_3$ (alkaline hydrolysis); PNK (polynucleotide kinase-treated $HCO_3$ lane).

Figure 3:
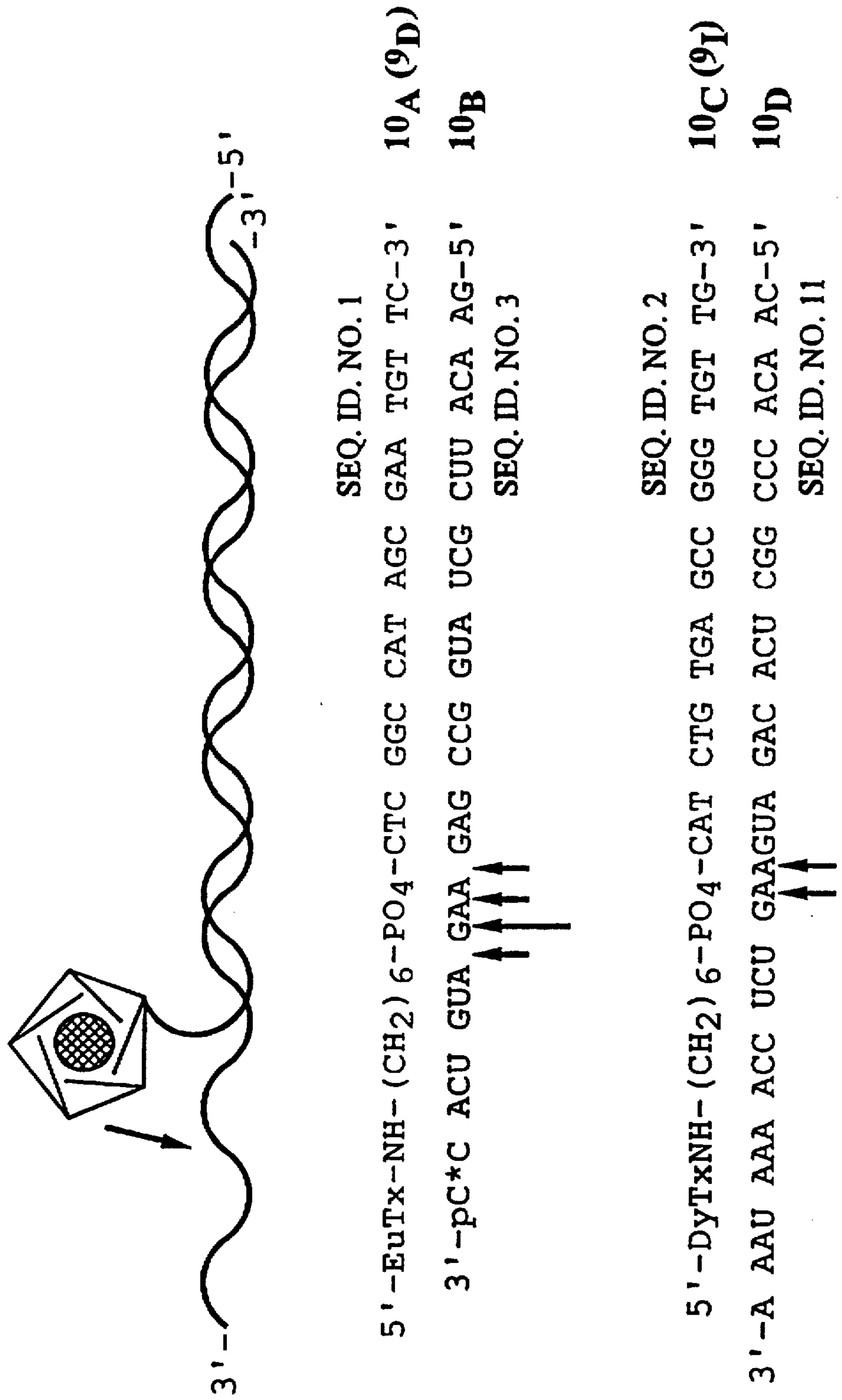
FIG. 3 shows a schematic representation of cleavage of an RNA 31-mer by EuTx-DNA conjugate and of an RNA 36-mer by DyTx-DNA conjugate; the arrows show sites of metal-catalyzed hydrolysis.

As illustrated schematically in FIG. 3, ca. 30% cleavage occurred near the expected location of the Eu-texaphyrin complex upon hybridization with conjugate $100_A$. Cleavage yield was measured by densitometry and calculated as ratio of cleavage band to intact material. The corresponding cleavage bands were not observed when this same substrate was incubated with oligonucleotides that were non-complementary in sequence, unmodified, or were modified internally with the complex. Control reactions indicated that ambient light, calf thymus DNA or type of buffer (Tris acetate or HEPES, EDTA, pH 6.0–8.0) had no apparent effect on cleavage efficiency. EDTA inhibits cleavage by free lanthanide(III) cations as observed in Morrow et al. (1992).

Hydrolysis of 5'-end labelled RNA 30-mer $10_B$ by conjugate $10_A$ (a 5' EUTx conjugate having an oligonucleotide complementary to substrate $10_B$) was demonstrated, following the above procedures. Test 1: 5'-End labelled RNA 30-mer $10_B$ substrate was incubated with 2.5 μM EuTx-DNA conjugate $10_A$ ($9_D$) for 24 hr at 37° C. (lanes 3–6) or 25° C. (lanes 7–14) in buffers containing 100 mM NaCl. Key: lane 1, non-incubated RNA control; lane 2, ribonuclease T1 (G) reaction; lanes 3, 8, 50 mM HEPES, pH 7.5, 25 μM EDTA; lanes 4, 9, 50 mM HEPES, pH 7.0, 25 μM EDTA; lane 5, 10:50 mM TrisAcetate pH 7.5, 25 μM EDTA; lanes 6,11,14, 50 mM TrisAcetate pH 7.0, 25 μM EDTA; lane 7, 50 mM HEPES, pH 7.5; lanes 12, 13, 50 mM TrisAcetate, pH 7.0; lane 13, 5 μM Fe(II), 4 mM DTT, 5 μM non-modified oligo $9_E$; lane 14, no conjugate control. Test 2: 5'-End labelled RNA 30-mer $10_B$ substrate was incubated for 25 hr at 37° C. in 50 μm HEPES (or TrisAcetate, lane 6) buffer containing 100 mM NaCl, 25 μM EDTA, and 5 μg/mL calf thymus DNA. Key: lane 1, no DNA control; lane 2, non-modified oligodeoxynucleotide $9_E$ (2.5 μM); lane 3, $9_B$ (2.5 μM); lane 4, $9_C$ (2.5 μM); lanes 5–9, $9_D$ ($^{10}{}_A$) (250 nM). Comparison of lanes 3–6 with lanes 7–14 of the Test 1 gel indicated that hydrolysis occurred more readily at 37° C. than at 25° C. Lane 3 of the Test 2 gel demonstrated that a noncomplementary oligo $9_B$ did not effect hydrolysis of $10_B$ and lane 4 of the Test 2 gel demonstrated that a conjugate having a complementary oligo and EuTx bound to an internal T residue did not effect hydrolysis of the RNA substrate. Lanes 5–9 of the Test 2 gel demonstrated hydrolysis of the RNA substrate by $10_A$.

The cleavage fragments co-migrated with bands in sequencing lanes produced by incubation of substrate under alkaline conditions or subjected to partial digestion with a series of base-specific ribonucleases (For an example of a similar end-product analysis, see Dange et al., 1990). This observation is consistent with a hydrolytic mechanism, presumably involving the EuTx acting as a Lewis acid that facilitates an intramolecular attack of the 2'-hydroxyl group to effect cleavage. There were bands indicating site-specific cleavage of the ribonucleotide target sequence in the absence of any added cleavage reagents. Although the source of this background cleavage is unknown, it is believed to be the direct result of a higher order structure (ie., a hairpin) of the oligoribonucleotide, since hybridization with any complementary oligonucleotide dramatically inhibited the cleavage. This type of structure-dependent cleavage behavior has been seen previously with oligoribonucleotides (Dange et al., 1990, Kazabov et al., 1992).

Maximal cleavage activity of the EuTx-oligonucleotide was observed down to 25 nM conjugate. Decreased cleavage below this level may be due to a decrease in hybridized material (as judged by increased background cleavage of the target RNA present at a concentration of about 1 nM). By means of comparison, the free europium complex non-specifically hydrolyzed the RNA substrate at 25 μM. In the control reaction containing both complex and the non-derivatized complementary DNA oligomer, cleavage occurred predominantly in the single-stranded region, although still at lower efficiency than the EuTx-DNA conjugate at 2.5 nM. Thus, attachment of the EuTx to the DNA probe increases its effective concentration ca. 10,000-fold. A target RNA without the secondary structure observed here would likely allow for cleavage at lower DNA-EuTx concentrations. These data indicate the utility of such conjugates in antisense applications.

As demonstrated in the present example, the selectivity of the texaphyrin complexes is enhanced by covalently linking oligonucleotides onto the periphery of the macrocycle. Since the metal complexes do cleave RNA over DNA preferentially, the DNA appendages would remain intact during the hydrolysis experiments. The DNA arm will recognize and bind to an appropriate RNA segment, effectively increasing the metal concentration at these loci relative to the overall metal concentration in solution. Phosphate ester hydrolysis will therefore be significantly increased at specific locations along the RNA backbone. In one embodiment, primers (known or deduced) for PCR could be coupled to a hydrolytic divalent or trivalent texaphyrin complex to induce hydrolysis of proximal RNA.

Figure 4A:
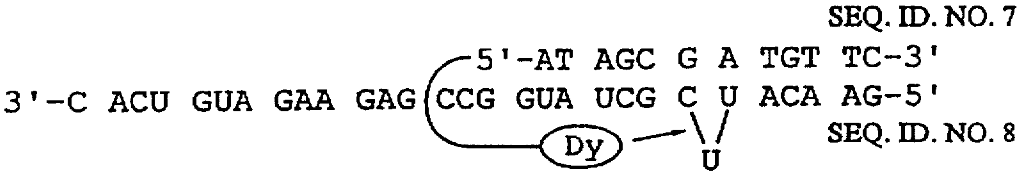
FIGS. 4A and 4B show examples of the oligonucleotide conjugate having a one-base deletion and, therefore, causing the substrate to have a one-base loop with enhanced susceptibility to hydrolysis.
Figure 4B:
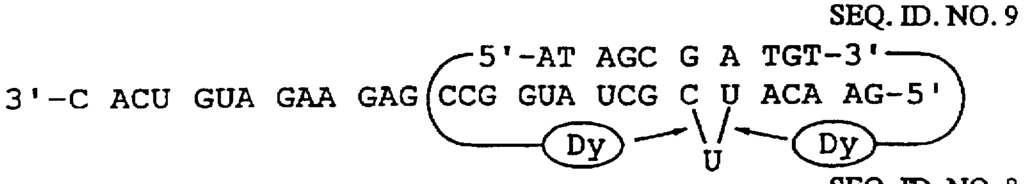

Enhancement of RNA hydrolysis by the metallotexaphyrin complex-conjugate may be accomplished by designing the deoxyribonucleotide to bind to the RNA target so as to produce a single-stranded loop which may have increased susceptibility to hydrolysis. The loop may contain one or more nucleotides. In this case, the oligodeoxyribonucleotide acts as a catalytic group by using the energy of its binding to the RNA target to increase the ground state energy of the targeted phosphate diester. Examples are illustrated in FIGS. 4A and 4B. FIG. 4A shows a DNA twelve-mer lacking a nucleotide to base pair with the looped out "U" and conjugated at its 5' end to a Dy(III) texaphyrin complex. Binding to the RNA substrate causes a one-base loop structure that is a site of enhanced susceptibility to hydrolysis by the Dy(III) Txp complex. FIG. 4B shows a DNA ten-mer lacking the same nucleotide, conjugated to a Dy(III)Txp at its 3' end and to a second Dy(III)Txp at its 5' end, binding to the RNA substrate so as to cause the same one-base loop structure. The loop is a site of enhanced susceptibility to hydrolysis, this time by the two Dy(III)Txp complexes which converge on the loop structure upon binding. In this example, one Dy(III)Txp may act as a general acid and the second may act as a general base via a Dy(III)Txp-bound hydroxyl group for activating the RNA towards hydrolysis.

EXAMPLE 4

Site-Specific Hydrolysis of RNA by Dysprosium (III)-Texaphyrin and Europium(III)-Texaphyrin Conjugated to Synthetic Oligodeoxyribonucleotides of Varying Lengths Following the procedures of Example 3, oligodeoxyribonucleotide-amines of varying nucleotide lengths and modified at the 5' end (obtained from Keystone Labs, Menlo Park, Calif.) were reacted with carboxylic acid functionalized dysprosium(III)-texaphyrin complex $8_B$ to give DyTx-oligo conjugates $9_F$–$9_I$ (FIG. 2) Corresponding EuTx-oligo conjugates were also prepared.

Each of the above-described conjugates was then incubated with the 3'-labeled synthetic RNA 30-mer $10_B$ following the procedures of Example 3. Labelled substrate ((5'-end labelled RNA 30-mer $10_B$ (lanes 1–9) or 36-mer $10_D$ (lanes 12–18)) was incubated with or without 250 nM conjugate for 24 h at 37° C. in buffer containing 100 mM NaCl, 50 mM HEPES pH 7.5, 25 μM EDTA. They were then placed on a 20% denaturing polyacrylamide gel. Key: lanes 1, 12, no conjugate, control; lanes 2, 6, 13, $9_B$; lanes 3, 7, 14, $9_D$; lanes 4, 8, 15, $9_I$; lanes 5, 9, 16, $9_H$; lanes 10, 17, $HCO_3$, sequencing; lanes 11, 18, base-specific ribonuclease U2 (A) sequencing. Reactions corresponding to lanes 1–5 were conducted under inert (argon) atmosphere, while reactions corresponding to lanes 12–16 were conducted under oxygen. All of the conjugates having complementary DNA and a texaphyrin complex at either end of the oligo hydrolytically cleaved the RNA, although the RNA was hydrolyzed by the Dy conjugates at about twice the rate (producing ca. 60% cleavage of the RNA) as by the Eu conjugates. At the 250 nM concentration of DNA used, the 12-mer conjugate was found to be as effective as the 20-mer conjugate, the 9-mer conjugate was less effective and only a small amount of cleavage was observed with the EuTx-9 mer conjugate. Increased background cleavage of the RNA substrate in the presence of the 9-mer conjugate indicates a lower degree of binding by the shorter oligonucleotide.

These data indicate that oligonucleotides having as few as 12 bases provide the specificity needed for accurate and full hydrolytic activity. This aspect is important for drug design, since the ability of an oligonucleotide analog to traverse a cellular membrane is generally found to be inversely proportional to its length.

EXAMPLE 5

Site-Specific Hydrolysis of a 36-Mer RNA by Dysprosium(III)-Texaphyrin Conjugated to a Synthetic Oligodeoxyribonucleotide A 3'-labelled synthetic RNA 36-mer $10_D$ (Promega Corp., Madison, Wis.) (FIG. 3) was incubated with an excess of the DyTx-oligo conjugate $10_C(9_I)$, following the procedures of Example 3, and the hydrolysis observed. As illustrated schematically in FIG. 3, the DyTx-oligo conjugate hydrolyzed the RNA at positions indicated by the arrows. This additional result supports the breadth of utility for the texaphyrin-oligonucleotide conjugates in the hydrolysis of ester bonds.

EXAMPLE 6

Synthesis of Texaphyrin-Oligonucleotide Conjugates Having a Texaphyrin Attached to the 3' end of the Oligonucleotide Two oligodeoxyribonucleotides of 12 bases each were synthesized to contain alkylamine groups at the 3' terminal phosphate (Keystone Labs, Menlo Park, Calif.). These oligomers were reacted with carboxylic acid functionalized Eu(III)-texaphyrin complex $8_B$ or a Lu(III)texaphyrin functionalized complex corresponding to $8_B$ following the procedures of Example 3, to give conjugates $9_J$, $9_K$ and $9_N$ (FIG. 2).

These 3'-conjugates may be of particular importance in certain embodiments of the present invention, since attachment of large groups (such as the present texaphyrin complexes) to the 3' end of oligonucleotides renders the oligonucleotide resistant to cellular nucleases.

In a similar manner, an embodiment of the present invention is the addition of particular ligands to the 3' end of an oligonucleotide having its 5' end conjugated to a texaphyrin. The function of the 3' ligand is to aid in the uptake of the conjugate into the cell. Such ligands are known in the art and include, but are not limited to, cholesterol and polylysine.

A further embodiment of the present invention in the hydrolysis of RNA using metallotexaphyrin complex-oligonucleotide conjugates is the use of a set of two conjugates, one having the metallotexaphyrin complex conjugated to the 5' end of an oligomer and the other having a metallotexaphyrin complex conjugated to the 3' end of an oligomer and the oligomers are complementary to the same RNA substrate, one just upstream from the other, so as to position both metallotexaphyrin complexes in proximity to the targeted hydrolysis site as depicted in FIG. 5. The distance separating the two catalytic groups may be varied by preparing a nested set of oligomer-5'-conjugates of varying lengths and comparing the hydrolysis efficiencies that result upon the simultaneous binding of the two conjugates to the RNA template.

EXAMPLE 7

Synthesis of an Eu(III) Texaphyrin-Oligonucleotide Dual Conjugate

An oligodeoxyribonucleotide having 12 bases was synthesized to contain alkylamine groups at both the 3' and the 5' ends (Keystone Labs, Menlo Park, Calif.). This oligomer was reacted with an excess of the carboxylic acid functionalized Eu(III)-texaphyrin complex $8_B$, following the procedures of Example 3, to give the dual conjugate $9_L$ (FIG. 2) which has an Eu(III)Tx metal complex at both the 3'- and the 5'-ends of the 12-mer.

The use of two texaphyrin-metal complexes conjugated to the same oligonucleotide, one at each end, should effect the hydrolysis of RNA with increased efficiency due to the concerted activity of the metal complexes. In this embodiment, it is preferred that both of the texaphyrin complexes contain the same metal, preferably yttrium or a lanthanide metal cation and more preferably Y(III), Eu(III) or Dy(III). One of the metallotexaphyrin complexes may act as an acid and the second may act as a base in order to further activate the RNA towards hydrolysis.

Further, a dual conjugate provides versatility in the functions that may be accomplished by this one molecule. For example, the oligonucleotide provides binding specificity, one metallotexaphyrin complex may provide for imaging (having Gd(III) as the metal ion, for example) while the other provides for phosphate ester hydrolysis. Such a dual conjugate allows for two functions, imaging and hydrolysis, to be effected by one molecule.

The use of metallotexaphyrin complexes to cleave RNA in vivo as a treatment procedure relies on the effective localization of the complex to the site of desired cleavage. A site of desired cleavage may be a position novel to undesired organisms in terms of health care. A site of desired cleavage may be a messenger RNA encoding a product deleterious to the host or may be a normal RNA that is deleterious in some way.

EXAMPLE 8

Sequence-Specific Inhibition of Cell Proliferation by Dy(III) Texaphyrin Conjugated to a 15-mer Phosphorothioate The present example provides for the enhancement of antiproliferative activity of a 15-mer phosphorothioate directed toward an oncogene target (c-myc) which is observed upon conjugation to Dy(III)Tx (cpd. $8_C$ where the metal is Dy). In general terms, a human promyelocytic leukemia cell line (HL-60, purchased from ATCC, Rockville, Md.), maintained under conditions of exponential growth, was incubated in the presence or absence of an oligonucleotide test species. At periodic intervals (after 4 and 7 days) an aliquot of cells was removed from culture and the number of viable cells was quantitated using a calorimetric assay based on mitochondrial processing of dye (MTT), following the procedures of Mosmann, T., *J Immunol. Methods*, 65 (1983) 55–63.

HL-60 cells were maintained in exponential growth by adding fresh media (RPMI-1640, 10% FCS, L-glutamine) every 3–5 days. Stock cells were diluted with media to 40,000 cells/mL and incubated for 24 h, whereupon 0.9 mL of diluted cells were pipetted into each well on a 24-well culture plate. Additions of oligonucleotide test species $11_A$, $11_B$ or $11_C$ were made from 100μM solutions, and DEPC-treated water was added to achieve a final volume of 1 mL within each well.

| | |
|---|---|
| 5'-H$_2$—(CH$_2$)$_6$—PSO$_3$—GAG GCT GCT GGT TTT-3'  $11_A$ | SEQ. ID NO. 17 |
| 5'-DyTxHN—(CH$_2$)$_6$—PSO$_3$—GAG GCT GCT GGT TTT-3'  $11_B$ | SEQ. ID NO. 17 |
| 5'-DyTxHN—(CH$_2$)$_6$—PSO$_3$—CAT CTG TGA GCC GGG-3'  $11_C$ | SEQ. ID NO. 18 |

Conjugate $11_B$ was compared side-by-side with its non-conjugated analogue $11_A$ on each of three 24-well plates, at 5, 2.5 and 1.25 μM concentrations, respectively. Conjugate $11_B$ was also compared side-by-side with the sequence-nonspecific conjugate $11_C$ on each of three 24-well plates, at 5, 2.5 and 1.25 μM concentrations, respectively. Each species was tested in triplicate. The 24-well plates were incubated at 37° C. under a 5% carbon dioxide atmosphere.

The concentration of cells in each well was determined at four days and at seven days using an MTT assay. Prior to sampling, each well was mixed by aspiration with a sterile pipette tip (P1000). A 75 mL aliquot was removed from three wells using a multichannel pipettor and transferred to a 96-well plate. Two aliquots were removed in this way, resulting in six wells overall on the 96-well plate for each test species. To each well, 25 μL of MTT dye (2 mg/mL in RPMI-1640, L-glutamine, without phenol red) was added, and the reactions were incubated for 2–4 h at 37° C. Before reading the absorbance of each well on a microplate reader (Molecular Devices, Sunnyvale, Calif.), 200 μL of a solution (0.04M HCl in isopropyl alcohol, 10 vol % Tween-20) was added to dissolve the precipitated dye, and the wells were mixed by aspiration. Absorbance was read at 570 nm and 650 nm, with the latter reading used for a background subtraction. A set of standards, prepared from untreated cells by serial dilution, was run on each microplate in order to construct a calibration curve.

Figure 6:
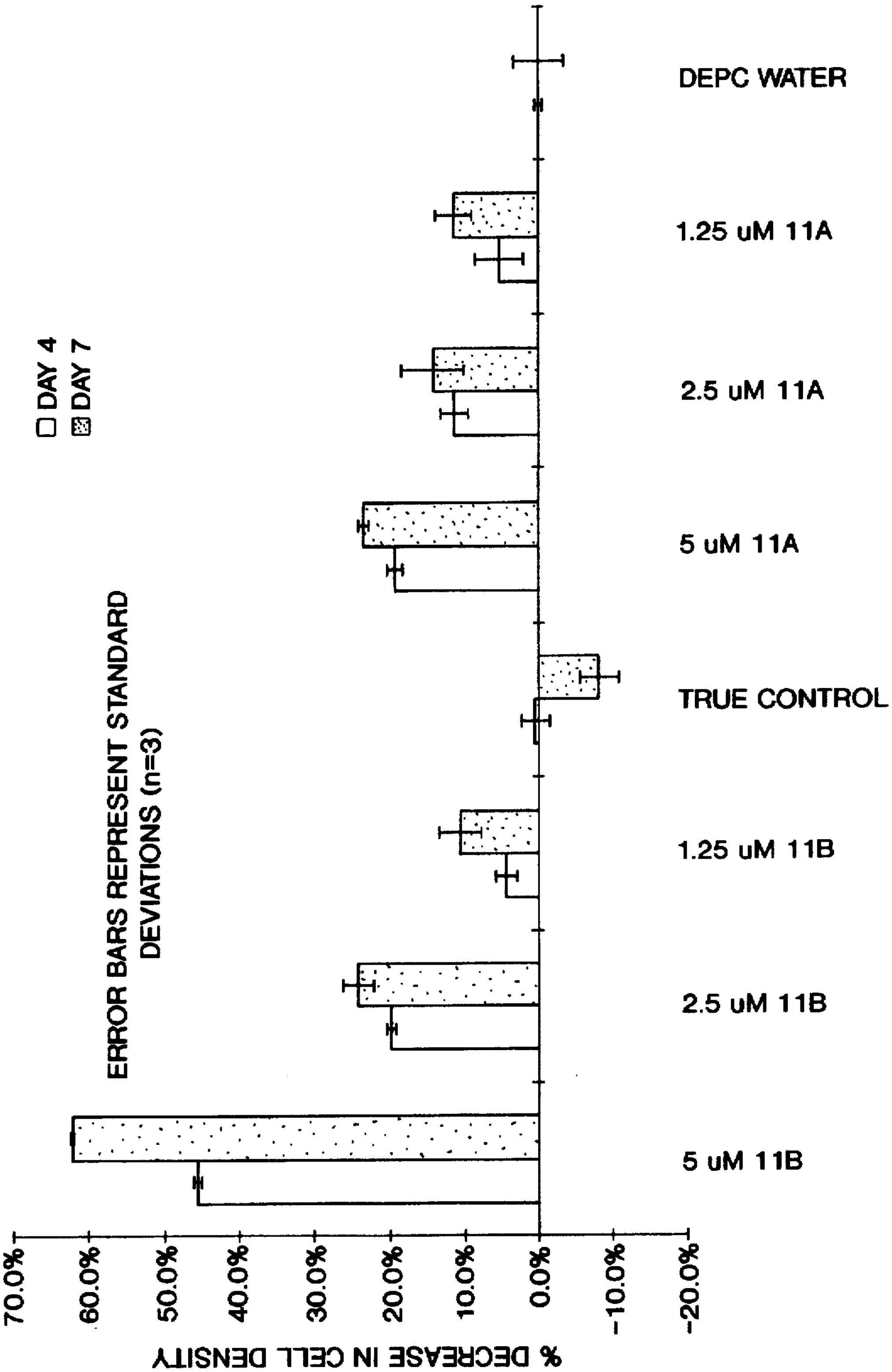
FIGS. 6 and 7 show the inhibition of cell proliferation by DyTx-oligonucleotide conjugates.
Figure 7:
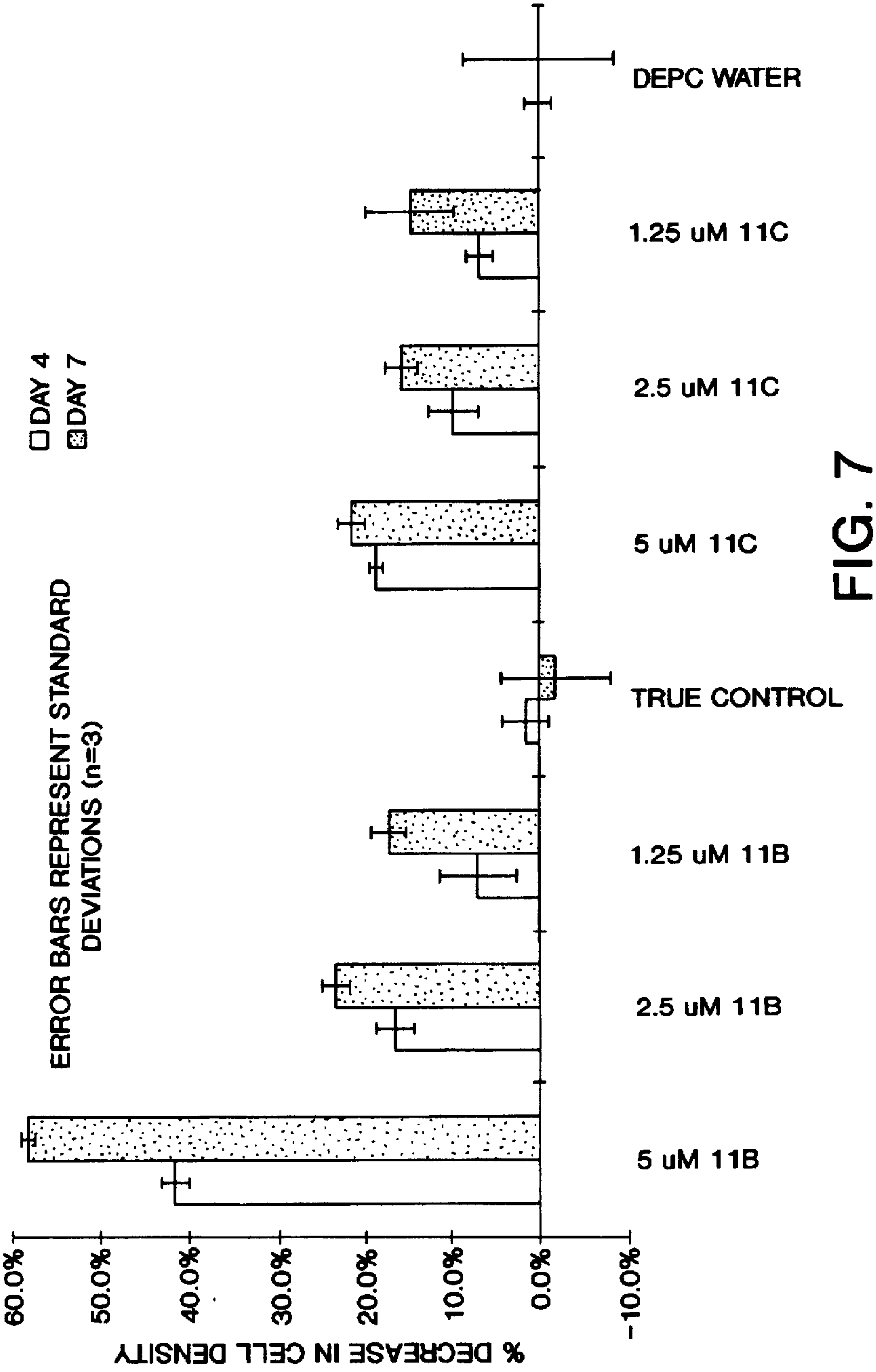

Data comparing conjugate $11_B$ and non-conjugated analogue $11_A$ are presented in FIG. 6; data comparing conjugates $11_B$ and $11_C$ are presented in FIG. 7. Data for each test species are plotted as decrease in cell density relative to a control of DEPC-treated water.

In this example, the antiproliferative activity of a 15-mer phosphorothioate oligonucleotide conjugated with DyTx was compared with the activity of the non-derivatized analogue of the same sequence and, in an independent experiment, with the activity of a 15-mer phosphorothioate conjugate which is sequence-nonspecific for the targeted RNA. In all cases, the phosphorothioates displayed a significant background level of sequence-nonspecific inhibition of cell growth. However, the antisense conjugate $11_B$ shows a dose-dependent activity beyond this which is significantly greater than that of either the non-derivatized antisense agent $11_A$ or the sequence-nonspecific conjugate $11_C$. These observations are consistent with a model whereby conjugation to DyTx facilitates the ability of a phosphorothioate oligomer to interfere sequence-specifically with the expression of an oncogene product, thereby inducing the terminal differentiation of a cancerous cell line. The probable mechanisms responsible for this enhancement of antisense activity include improved uptake of the texaphyrin-conjugate by the cells, better intracellular targeting of the agent, and/or site-specific hydrolysis of the c-myc messenger RNA by the DyTx upon hybridization.

The data of Examples 1 through 8 demonstrate that texaphyrin-metal complexes may be developed into RNA antisense reagents. The antisense approach is efficient in regulating the expression of proteins. Many copies of a particular polypeptide or protein are made from one messenger RNA molecule; therefore, by moving up in the levels of cellular processes and knocking out the message (the mRNA), fewer attacking agents would be required because there would be fewer target sites. The production of protein by an organism could be efficiently and effectively modulated. The antisense strategy provides a clear and rational method for new drug design because there is one requirement, that the antisense probe hybridize to its target molecule. The hybridization requirement is very well understood via complementary Watson-Crick base pairing. Unlike the present methods in the art which require screening of thousands of compounds and X-ray crystal structure analysis, the information needed for antisense technology is the sequence of the target. Treating native RNA with these texaphyrin complex-oligonucleotide conjugates results in the texaphyrin conjugate binding to a complementary RNA sequence via an appended oligonucleotide. The texaphyrin complex then cleaves the RNA proximal to this specific site. Either one or two texaphyrin molecules may be attached to the DNA, creating the potential for gene splicing reagents.

The texaphyrin oligo conjugate would have immediate applications for in vitro, ex vivo or in vivo anti-viral and anti-bacterial therapy as well as cancers (an oligonucleotide complementary to an oncogene, for example) and inflammatory responses that are caused by the overexpression of certain proteins. Antisense technology is discussed in U.S. Pat. Nos. 5,194,428, 5,110,802 and 5,216,141, all of which are incorporated by reference herein.

EXAMPLE 9

Texaphyrin-Sapphyrin Conjugates for Ester Cleavage and Transport Across Membranes A further means of gaining selectivity is to link covalently the texaphyrin complex to a sapphyrin (sap) molecule. Sapphyrins are disclosed in, e.g., Sessler et al., 1992; Furuta et al., 1991; Sessler et al., 1991; U.S. Pat. No. 5,159,065; U.S. Pat. No. 5,120,411; U.S. Pat. No. 5,041,078, all incorporated by reference herein. Since sapphyrins bind phosphate, K=20 $M^{-1}$ in water at pH 7, the linked texaphyrin-sapphyrin complex (txp-sap) could effectively increase the metal concentration at locations adjacent to the sapphyrin binding sites. Since the txp-sap molecule would be quite large, it is expected that the ternary structure of RNA will provide a limited number of favorable binding sites. Thus, a degree of structural selectivity for RNA hydrolysis would be expected, with this selectivity being based on the conformations of the substrate molecules.

The synthesis of (Eu) texaphyrin-sapphyrin conjugate

Synthesis was accomplished by amide bond formation between activated (Eu)texaphyrin carboxylic acid and amino-substituted sapphyrin. By the same strategy, a variety of texaphyrin-sapphyrin conjugates may be prepared including conjugates where other metallic cations may be incorporated into the texaphyrin moiety, as well as conjugates of texaphyrins with ligands other than sapphyrin. The formation of exemplary amide-linked derivatives of texaphyrin is illustrated below. R=sapphyrin, texaphyrin, porphyrin, a catalytic group, or amine-containing substituents such as amine-containing saccharides, polysaccharides, amino acids, amino acid derivatives, polyamino acids and the like; n=1–7; $(NH_2)_m$ represents monoamines $NH_2(CH_2)_x$, x=0–12; diamines $NH_2—(CH_2)_x—NH_2$, x=2–12; triamines $(NH_2(CH_2)_x)_3N$, x=2–6; or tetra $(NH_2(CH_2)_x)_2N(CH_2)_yN((CH_2)_xNH_2)_2$, x=2–4, y=2–6.

with zeolite (by standard procedure for removing free europium salt). The product was twice precipitated from methanol by adding diethylether. The collected dark green solid was dried under high vacuum overnight. Yield 91.0%. Characterization data: Elemental analysis for $C_{38}H_{44}N_5O_5Eu.2(OAc)$ (F.W. 920.855) calc. 54.78% C, 5.47% H, 7.61% N; found 54.46% C, 5.50% H, 7.55% N. FAB HR MS: For $C_{38}H_{43}N_5O_5Eu$ calc. 802.24626; found 802.247752. UV-Vis (EtOH, $\lambda_{max}$): 420, 469, 760 nm.

The Synthesis of EuTexaphyrin-Sapphyrin derivative (($16_C$, R=$(CH_2)_3OH$, M=Eu(III), n=3)): The aminosapphyrin derivative 3,8,17,22-tetraethyl-12-[N-(2-aminoethyl) aminocarbonylethyl-2,7,13,18,23-pentamethylsapphyrin ($16_A$) was prepared as follows: The corresponding sapphyrin monocarboxylic acid was, after activation with DCC, reacted with t-BOC monoprotected ethylenediamine and then subsequently deprotected by treating with TFA at room temperature for 1 hour.

Texaphyrin $16_B$ (0.092 g, 0.1 mmol) was dissolved in 10 mL dry dimethylformamide (solvent without

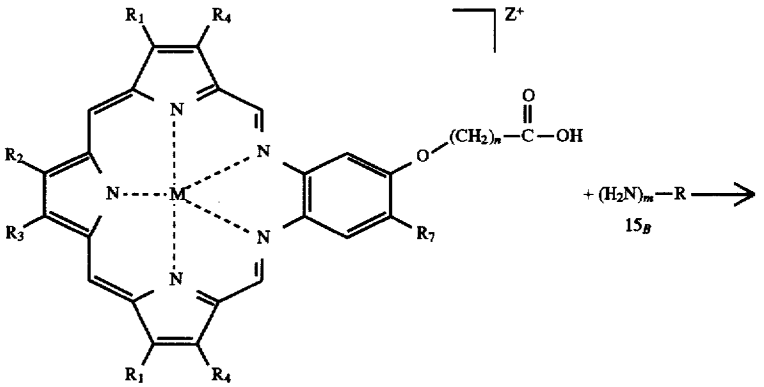

$15_A$

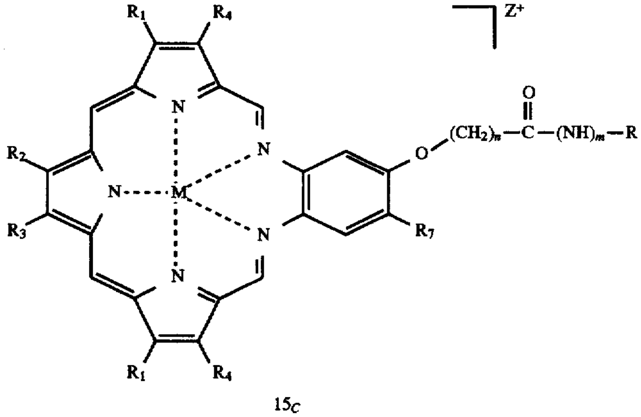

$15_C$

The synthesis of (Eu) texaphyrin acid EuT2B1 ($O(CH_2)_3CO_2H$) (($16_B$, R=$(CH_2)_3OH$, M=Eu(III), n=3)). The corresponding nonaromatic texaphyrin macrocycle.HCl (0.694 g, 1 mmol) was dissolved in 80 mL of dry methanol. $Eu(OAc)_3.H_2O$ (0.329 g, 1 mmol) was added, followed by triethylamine (0.5 mL). The reaction mixture was refluxed (reflux condenser was open to the air) for 6 hours, with the progress of metallation followed by visible spectra. Methanol was evaporated under reduced pressure to give a dry, dark solid which was washed with dichloromethane under vigorous stirring for 2 hours. The product was filtered off, redissolved in MeOH (25 mL), and the solution was treated dimethylamine), and the solution was cooled on ice to 0° C. The activating agent (carbodiimide, EDC, 95.5 mg, 0.5 mmol) and hydroxybenzotriazole (5 mg) were added and the mixture was held at 0° C. for 45 minutes. The solution of aminosapphyrin derivative $16_A$ (0.067 g, 0.1 mmol) in 5 mL of dimethylformamide and 0.1 mL of dry pyridine was added at the same temperature. The reaction mixture was kept at 0° C. for 30 minutes, allowed to warm to room temperature, and stirred for 3 days. Solvent was evaporated under reduced pressure. The crude product was washed, dissolved in EtOH (10 mL), and diethylether was slowly added. Precipitated product was dried in vacuo. Yield 68%.

Characterization data: UV-Vis $\lambda_{max}$ (EtOH): 358, 431, 450, 618, 681, 761 nm. ($H_2O$, pH7): 358, 408, 455, 623, 675, 765 nm. FAB MS: For $C_{80}H_{95}N_{12}O_5Eu$ calc. 1456.67539; found 1457.

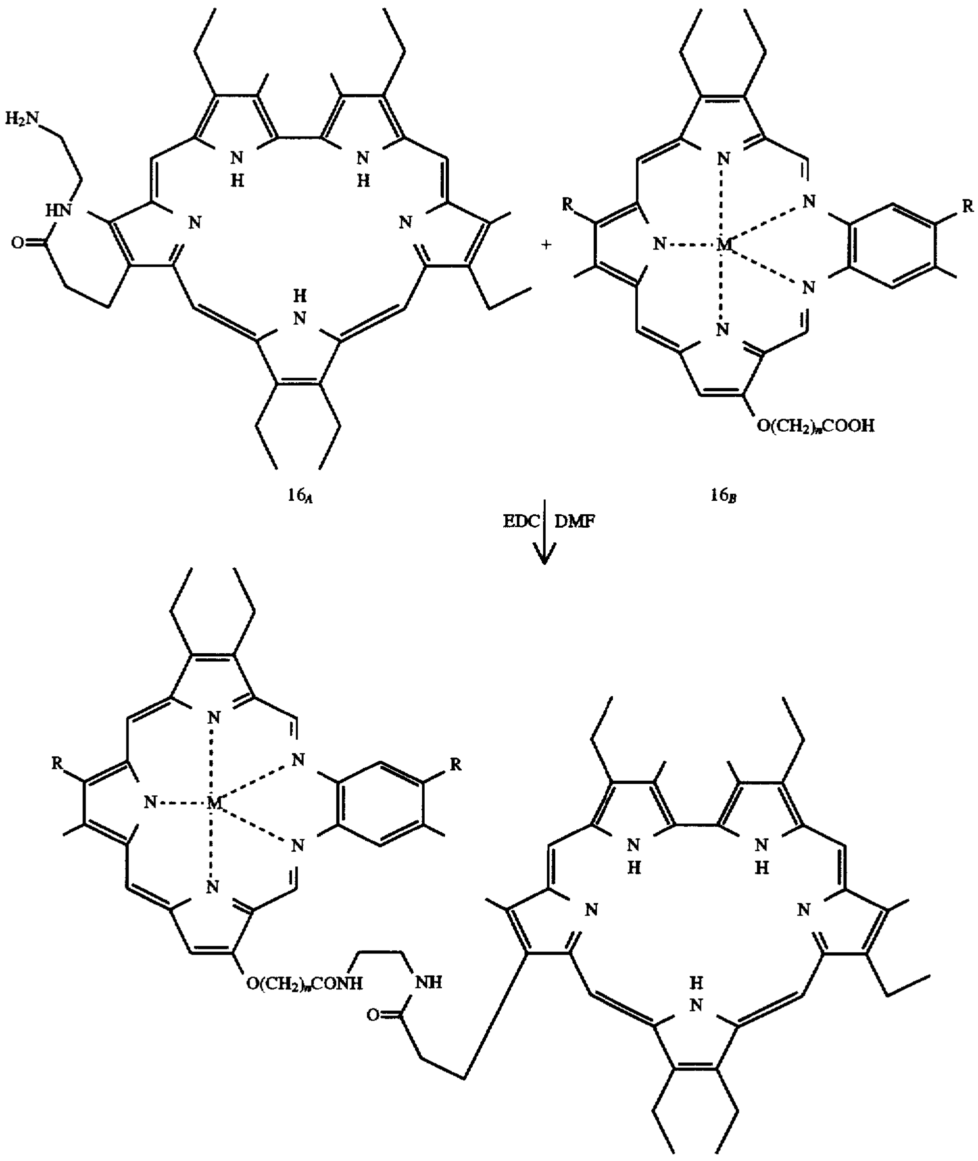

$16_A$ $16_B$ $16_C$

Alternative synthetic approaches to analogous heterodimers may include the coupling of amino-substituted texaphyrins ((prepared by the reaction of texaphyrin carboxylate anion with monoprotected ethylenediamine $H_2N(CH_2)_2NHR$, where R is $(CH_3)_3COCO$-(t-BOC), followed by heating to 180° C. to effect deprotection)) with activated sapphyrin monocarboxylic acid derivatives (e.g., sapphyrin acid chloride, or the products obtained from treatment with dicylohexylcarbodiimide, DCC)

Compound $16_C$ was tested (a) for transport of ADP and ATP across bulk liquid membrane—efficient transport at neutral pH was observed, and (b) for phosphodiester hydrolysis—during ATP transport, AMP was formed as a result of hydrolysis. Transport studies were performed using an $H_2O$—$CH_2Cl_2$—$H_2O$ three-phase Pressman-type U-tube type model membrane system (Araki et al., 1990). Aqueous phase I (source phase) was 5 mM solution of ADP, ATP at pH 7.0, the organic phase was 0.1 mmol solution of (Eu) texaphyrin-sapphyrin conjugate $16_C$. Aqueous phase II (receiving phase) was water, pH 7.0. The increase in concentration of ADP and ATP in the receiving phase as a result of membrane transport was followed as a function of time. Quantities transported were determined by HPLC analysis of receiving phase using cytosine and/or adenosine as the internal standard(s) (reverse phase analytical column, 10 mM phosphate buffer, pH 5.6). In this way the initial transport rates for the through-membrane transport of ADP and ATP were derived. Results showed that the initial rate of transport for ADP is in the range of $5\times10^{-9}$ mol/cm$^2$.hr, and about five times lower than this for ATP. During the course of the above-described through-membrane transport of ADP and ATP the formation of a new compound in the receiving phase, determined to be AMP by comparison with an authentic sample, was also observed. Since this AMP material was not present in the source phase nor observed when carrier-free control experiments were carried out, its production as the result of the (Eu)texaphyrin-sapphyrin conjugate mediated transport process is taken as indicating that the conjugate is capable of effecting the hydrolysis of a phosphoric anhydride bond.

Texaphyrin-sapphyrin conjugates or analogs thereof should be very useful in antisense applications: Sapphyrin binds to phosphate diesters, such as those of DNA, with high specificity and affinity. Certain metallotexaphyrin complexes bind to anionic phosphates and effect the hydrolytic cleavage of RNA and related species. Thus, a texaphyrin-sapphyrin conjugate should provide an enhanced recognition of RNA/DNA and an improved rate of hydrolysis by virtue of the induced "neighboring group effect".

Along with the potential to cleave RNA specifically, the texaphyrin molecule may be designed to pass through cell membranes and selectively attack viral RNA. Such a molecule would have the potential to treat human patients infected with a variety of viruses, including HIV, and to treat blood in vitro or ex vivo for viral infection to purge or purify blood.

EXAMPLE 10

Further Uses for Texaphyrin-Metal Complexes Coupled to Site-Directed Molecules Many cell membranes are partially constructed from phospholipids. Thus, metallotexaphyrin complexes may be developed into synthetic specific phospholipases. One skilled in the art in light of the present disclosure could then determine precisely the lipid side chain that is connected via the phosphate ester bond in a given phospholipid. An extension of this process would be to digest cell membrane components such as phosphatidyl choline and sphingomyelin. This is important since the latter participates in nerve and brain functions.

The present invention may be developed into a probe, a reagent or an assay for in vitro use in the detection, characterization or quantitation of a specific RNA sequence or of other phosphate-containing molecules.

The development of potent cytotoxins from metallotexaphyrin complexes may be accomplished by developing reagents that specifically hydrolyze phosphoric anhydrides such as ATP, ADP, NADH, or $FADH_2$. These cytotoxins may disrupt, in a biologically specific way, the flow of free energy in the cell and essentially starve the organism. This could allow for the death of undesired plants and animals or the treatment of mammalian cancers.

Liver diseases causing the accumulation of glycogen may be treated by hydrolyzing uridine diphosphate glucose (UDP), the phosphodiester precursor to glycogen. The present invention demonstrates that uridine phosphates are hydrolytically cleaved by metallotexaphyrin complexes and previous work with metallotexaphyrins (U.S. Pat. No. 5,252,720) has shown that they localize in the liver. Thus, one skilled in the art would realize that the basic features of this approach have already been demonstrated by experiment.

Cyclic adenosine monophosphate (cAMP) is believed to play an important part in regulating various hormones. Hydrolyzing cAMP to the linear adenosine monophosphate (AMP) impedes certain hormone regulation. Texaphyrin complexes may therefore be used as hormone regulation drugs.

A further use for metallotexaphyrin complexes may be as hydrolysis reagents for the detoxification of di- and trialkyl phosphate esters. Alkyl phosphate esters have a wide range of uses including solvents in chemical reactions, insecticides (e.g., parathion) and chemical nerve gases (e.g., diisopropyl phosphofluoridate, DIPF). Hydrolysis and detoxification of these agents in the environment is often slow by natural processes. Developing catalysts for the hydrolysis of alkyl phosphate esters could greatly improve the lives of many people. Texaphyrin complexes could further be developed as treatment for patients that have been exposed to such nerve agents.

The following references are incorporated in pertinent part by reference herein.

REFERENCES

Agrawal, S., and Tang, J. Y., *Tetrahedron Letters*, 31:7541, 1990.
Araki, T. et al., *Liquid Membranes: Chemical Applications*, CRC Press, Boca Raton, 1990.
Basile, L. A. et al., *J. Am. Chem. Soc.*, 109:7550, 1987.
Breslow, Ronald and Huang, Deeng-Lih, *Proc. Natl. Acad. Sci. USA*, 88:4080, 1991.
Browne, Kenneth A. and Bruice, Thomas C., *J. Am. Chem. Soc.*, 114(13):4951, 1992.
Chin, Jik and Banaszczyk, Mariusz, *J. Am. Chem. Soc.*, 111:4103–4105, 1989.
Chin, Jik and Banaszczyk, Mariusz, *J. Am. Chem. Soc.*, 111:2724, 1989.
Chin, Jik et al. *J. Am. Chem. Soc.*, 111:186–190, 1989.
Chin, Jik and Zou, Xiang, *Can J. Chem.*, 65:1882, 1987.
Dange, et al., Science, 248:585–588, 1990.
Eichhorn, G. L.; Butzow, J. *J. Biopolymers*, 3:79–94, 1965.
Eckstein, F., Ed., *Oligonulceotides and Analogues*, IRL Press, NY, 1991.
England, T. E.; Uhlenbeck, *O. C. Biochemistry*, 17:2069–2076, 1978.
Furuta et al., *J. Amer. Chem. Soc.*, 113:6677, 1991.
Hayashi, N., et al., *Inorg. Chem.*, 32:5899–5900, 1993.
Hendry, Philip and Sargeson, Alan M., *J. Amer. Chem. Soc.*, 111:2521, 1989.
Kazakov, S.; Altman, *S. Proc. Natl. Acad. Sci. USA* 89:7939–7943, 1992.
Kim, Jung Hee and Chin, Jik, *J. Am. Chem. Soc.*, 114:9792–9795, 1992.
Kolasa, et al., *Inorg. Chem.*, 32:3983–3984, 1993.
Komiyama, Makoto et al., *J. Chem. Soc., Chem. Commun.*, pp. 640–641, 1992.
Kuchino, Y. *Methods in Enzymology*, 180:154–163, 1989.
Menger, F. M. et al., *J. Am. Chem. Soc.*, 109:2800, 1987.
Modak, Anil S. et al., *J. Am. Chem. Soc.*, 113:283, 1991.
Morrow, J. R. et al., *J. Am. Chem. Soc.*, 114:1903, 1992.
Morrow, et al., *Inorg. Chem.*, 32:4566–4572, 1993.
Mosmann, T, *J. Immunol. Methods*, 65:55–63, 1983.
Ranganathan, Darshan et al., *J. Chem. Soc., Chem. Commun.*, 4:337, 1993.
Schneider, et al., *Angew. Chem. Int. Ed. Engl.*, 32:1716–1719, 1993.
Sessler et al., *Synlett*, pp. 127, 1991.
Sessler, J. L. and Burrell, A. K., *Top. Curr. Chem. Rev.*, 161:179, 1991.
Sessler et al., *Tetrahedron*, 48:9661, 1992.
Shelton, Valerie and Morrow, Janet R., *Inorg. Chem.*, 30:4295, 1991.
Stern, Michael K. et al., *J. Am. Chem. Soc.*, 112:5357, 1990.
Sumaoka Jun et al., *J. Chem. Soc. Chem. Commun.*, pp. 1707–1708, 1992.
Chung, Yongseog et al., *Tetrahedron Letters*, 31:5413, 1990.
U.S. Pat. No. 5,159,065.

U.S. Pat. No. 5,120,411.
U.S. Pat. No. 5,041,078.
Wickstrom, E., Ed., *Prospects for Antisense Nucleic Acid Therapy of Cancer and AIDS*, Wiley-Liss, NY, 1991.

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A method for enhancing the therapeutic activity of an oligonucleotide in a cell, the method comprising:

contacting a targeted intracellular RNA in a cell with a metallotexaphyrin-oligonucleotide conjugate, the contact being under physiologic conditions and for a time sufficient to hydrolyze the phosphate ester bond of said targeted intracellular RNA, wherein the metallotexaphyrin of said metallotexaphyrin-oligonucleotide conjugate has catalytic activity for phosphate ester bond hydrolysis and the oligonucleotide of said metallotexaphyrin-oligonucleotide conjugate has complementary binding affinity to said targeted intracellular RNA.

2. A method for enhancing the therapeutic activity of an oligonucleotide in a cell, the method comprising:

contacting a targeted intracellular RNA in a cell with a metallotexaphyrin-oligonucleotide conjugate, the contact being under physiologic conditions and for a time sufficient to hydrolyze the phosphate ester bond of said targeted intracellular RNA, wherein the metallotexaphyrin of said metallotexaphyrin-oligonucleotide conjugate has catalytic activity for phosphate ester bond hydrolysis and the oligonucleotide of said metallotexaphyrin-oligonucleotide conjugate has complementary binding affinity to said targeted intracellular RNA;

where the metallotexaphyrin-oligonucleotide conjugate has the following structure:

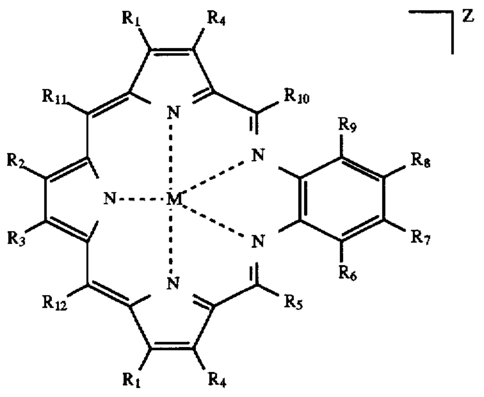

M is a divalent or a trivalent metal cation catalyzing phosphate ester bond hydrolysis in aqueous solution;

$R_1$–$R_4$, $R_7$ and $R_8$ are independently hydrogen, halide, hydroxyl, alkyl, aryl, haloalkyl, nitro, formyl, acyl, hydroxyalkyl, oxyalkyl, oxyhydroxyalkyl, saccharide, carboxy, carboxyalkyl, carboxyamide, carboxyamidealkyl, aminoalkyl, sulfonatoalkyl, amidealkyl, aryl, a site-directed molecule, a catalytic group, or a couple to a site-directed molecule or to a catalytic group;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, oxyalkyl, oxyhydroxyalkyl, carboxyalkyl, carboxyamidealkyl or a couple to a saccharide to a site-directed molecule or to a catalytic group; and Z is less than or equal to 5;

where at least one of $R_1$–$R_{12}$ is a site-directed molecule or a couple to a site-directed molecule, and the site-directed molecule is an oligonucleotide having binding affinity to said targeted intracellular RNA.

3. The method of claim 2 wherein the catalytic group is imidazole, guanidine, an amino acid, an amino acid derivative, a polyamino acid, an amine-substituted saccharide or a metallotexaphyrin complex.

4. The method of claim 2 wherein the site-directed molecule is an oligonucleotide, a hormone, an antibody, a molecule having affinity for a biological receptor, or a sapphyrin molecule.

5. The method of claim 2 wherein the oligonucleotide is an oligodeoxyribonucleotide.

6. The method of claim 2 wherein the oligonucleotide is further conjugated to a catalytic group.

7. The method of claim 6 wherein the catalytic group is imidazole, guanidine, an amino acid, an amino acid derivative, a polyamino acid, an amine-substituted saccharide or a metallotexaphyrin complex.

8. The method of claim 6 wherein the catalytic group is a metallotexaphyrin complex.

9. The method of claim 2 wherein the oligonucleotide has complementary binding affinity for oncogenes.

10. The method of claim 2 wherein the oligonucleotide has complementary binding affinity for the targeted RNA in a region proximal to the phosphate ester bond being hydrolyzed.

11. The method of claim 2 wherein the oligonucleotide is an antisense oligonucleotide.

12. The method of claim 2 wherein one of $R_3$, $R_7$, and $R_8$ is an oligonucleotide or a couple to an oligonucleotide.

13. The method of claim 2 wherein one of $R_3$, $R_7$ or $R_8$ is $O(CH_2)_nCO$-oligonucleotide where n is 1–7.

14. The method of claim 2 wherein M is a lanthanide cation.

15. The method of claim 2 wherein M is Eu(III), Tb(III) or Dy(III).

16. The method of claim 2 wherein the targeted RNA is selected from the group consisting of viral, including retroviral, RNA; messenger RNA (mRNA); ribosomal RNA; RNA cofactors; transfer RNA; small nuclear RNA; and small cytoplasmic RNA.

17. The method of claim 2 wherein the targeted RNA is mRNA.

18. The method of claim 2 where the oligonucleotide is an oligoribonucleotide.

19. The method of claim 2 where the oligonucleotide is a derivatized oligonucleotide or an oligonucleotide analog.

20. The method of claim 2 where the oligonucleotide is a derivatized oligonucleotide and is selected from the group consisting of methylphosphonates, phosphotriesters, phosphorothioates, and phosphoramidates.

21. The method of claim 2 where the oligonucleotide is 2'-O-alkyl oligoribonucleotide.

22. The method of claim 2 where $R_1$ is $CH_2CH_3$ or $CH_2CH_2CH_2OH$; each of $R_2$ and $R_3$ is $CH_2CH_3$; $R_4$ is $CH_3$; each of $R_5$, $R_6$, and $R_9$–$R_{12}$ is H; $R_7$ is H, $CH_3$, $OCH_3$, $O(CH_2)_nCOOH$, $OCH_2CH_2CH_2OH$ or $O(CH_2CH_2O)_nCH_3$ where n is 1–7; and $R_8$ is an oligonucleotide or a couple to an oligonucleotide.

23. The method of claim 22 where $R_8$ is $O(CH_2)_nCO$-oligonucleotide where n is 1–7.

24. The method of claim 2 where M is a lanthanide metal cation; $R_1$ is $CH_2CH_3$ or $CH_2CH_2CH_2OH$; each of $R_2$ and $R_3$ is $CH_2CH_3$; $R_4$ is $CH_3$; each of $R_5$, $R_6$, and $R_9$–$R_{12}$ is H $R_7$ is H, $CH_3$, $OCH_3$, $O(CH_2)_nCOOH$, $OCH_2CH_2CH_2OH$ or $O(CH_2CH_2O)_nCH_3$ where n is 1–7; and $R_8$ is an oligonucleotide or a couple to an oligonucleotide.

25. The method of claim 24 where $R_8$ is $O(CH_2)_nCO$-oligonucleotide where n is 1–7.

26. The method of claim 24 where the targeted RNA is mRNA.

27. The method of claim 24 where the oligonucleotide is an antisense oligonucleotide.

28. The method of claim 2 where M is Y(III).

* * * * *

UNITED STATES PATENT AND TRADEMARK OFFICE

CERTIFICATE OF CORRECTION

PATENT NO. : 5,763,172

DATED : June 9, 1998

INVENTOR(S) : Darren Magda et al.

It is certified that error appears in the above-identified patent and that said Letters Patent is hereby corrected as shown below:

In claim 2,7th line from the end, after "charide" insert a comma.

In claim 24, line 3, after "is H" insert a semicolon.

Signed and Sealed this

First Day of September, 1998

Attest:

BRUCE LEHMAN

*Attesting Officer*

*Commissioner of Patents and Trademarks*